(12) United States Patent
Vaidyanathan

(10) Patent No.: US 11,964,157 B2
(45) Date of Patent: Apr. 23, 2024

(54) PROGRAMMING RANK INDEX FOR ELECTRICAL STIMULATION AND RECORDING

(71) Applicant: Medtronic, Inc., Minneapolis, MN (US)

(72) Inventor: Janardan Vaidyanathan, Thane (IN)

(73) Assignee: Medtronic, Inc., Minneapolis, MN (US)

( * ) Notice: Subject to any disclaimer, the term of this patent is extended or adjusted under 35 U.S.C. 154(b) by 535 days.

(21) Appl. No.: 17/117,955

(22) Filed: Dec. 10, 2020

(65) Prior Publication Data

US 2022/0184401 A1 Jun. 16, 2022

(51) Int. Cl.
*A61N 1/36* (2006.01)
*A61N 1/05* (2006.01)

(52) U.S. Cl.
CPC .......... *A61N 1/36185* (2013.01); *A61N 1/05* (2013.01); *A61N 1/36139* (2013.01)

(58) Field of Classification Search
CPC ... A61N 1/00; A61N 2/00; A61N 5/00; A61N 7/00; A61N 1/05; A61N 1/36185
See application file for complete search history.

(56) References Cited

U.S. PATENT DOCUMENTS

| | | | |
|---|---|---|---|
| 7,305,268 | B2 | 12/2007 | Gliner et al. |
| 8,918,184 | B1 | 12/2014 | Torgerson et al. |
| 9,498,628 | B2 | 11/2016 | Kaemmerer et al. |
| 9,713,722 | B1 * | 7/2017 | Astrom .............. A61N 1/36185 |
| 2011/0264165 | A1 * | 10/2011 | Molnar .............. A61N 1/36185 607/45 |
| 2015/0005842 | A1 | 1/2015 | Lee et al. |
| 2016/0250476 | A1 | 9/2016 | Kaemmerer et al. |
| 2017/0333720 | A1 | 11/2017 | Astrom et al. |
| 2018/0369590 | A1 | 12/2018 | Kaemmerer et al. |
| 2019/0336773 | A1 | 11/2019 | Hoeffer et al. |
| 2020/0029894 | A1 | 1/2020 | Gerber et al. |

OTHER PUBLICATIONS

Astrom et al., "Prediction of Electrode Contacts for Clinically Effective Deep Brain Stimulation in Essential Tremor," Stereotactic and Functional Neurosurgery, vol. 96, No. 5, Sep. 28, 2018, pp. 281-288.
Steigerwald et al., "Directional Deep Brain Stimulation," Neurotherapeutics, vol. 16, No. 1, Sep. 19, 2018, pp. 100-104.
Dembek et al., "Directional DBS Leads Show Large Deviations from their Intended Implantation Orientation," Parkinsonism and Related Disorders, vol. 67, Oct. 2019, pp. 117-121.
International Search Report and Written Opinion of International Application No. PCT/US2021/062023, dated Apr. 4, 2022, 12 pp.

* cited by examiner

*Primary Examiner* — Mallika D Fairchild
*Assistant Examiner* — Thien Jason Tran
(74) *Attorney, Agent, or Firm* — Shumaker & Sieffert, P.A.

(57) ABSTRACT

A system includes processing circuitry configured to determine, for each respective electrode of a plurality of electrodes, a score based on a ratio of an electrical efficiency for the respective electrode to a therapeutic window for the respective electrodes. The processing circuitry is further configured to determine, based on the score of each respective electrode, a ranking of the plurality of electrodes, and to select, based on the ranking, a subset of the plurality of electrodes for delivery of electrical stimulation therapy.

20 Claims, 11 Drawing Sheets

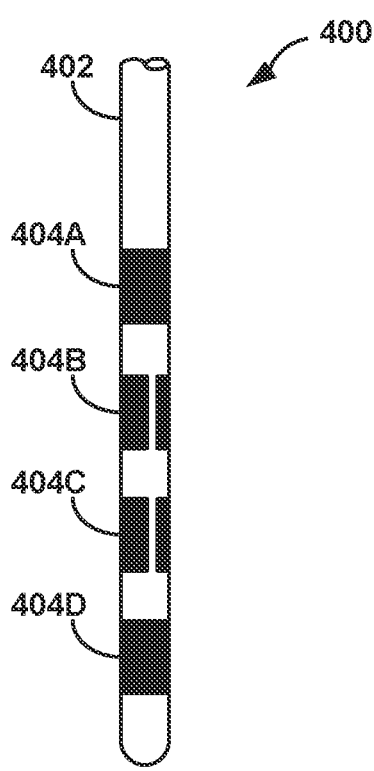
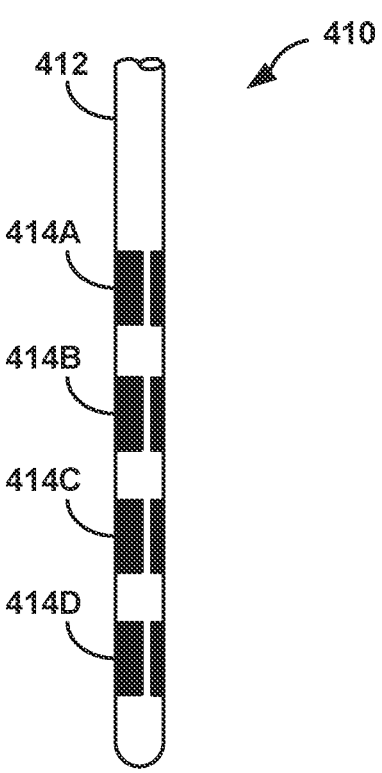
FIG. 4A
FIG. 4B

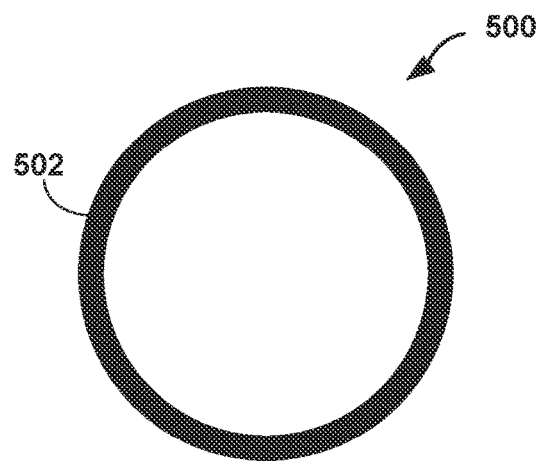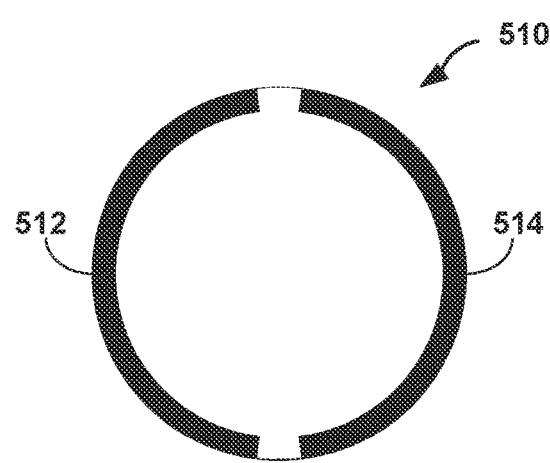
FIG. 5A  FIG. 5B
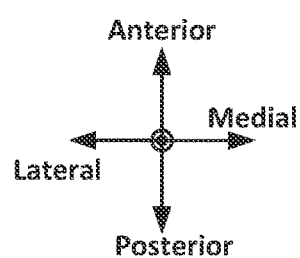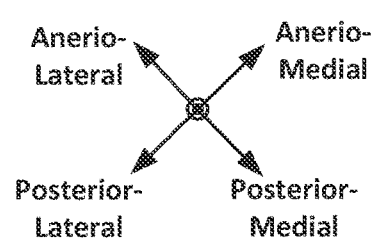
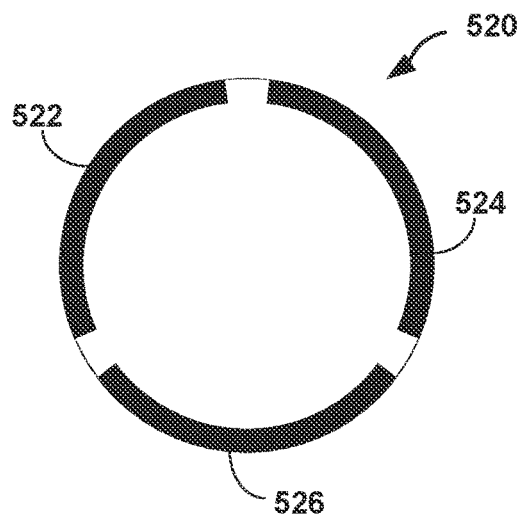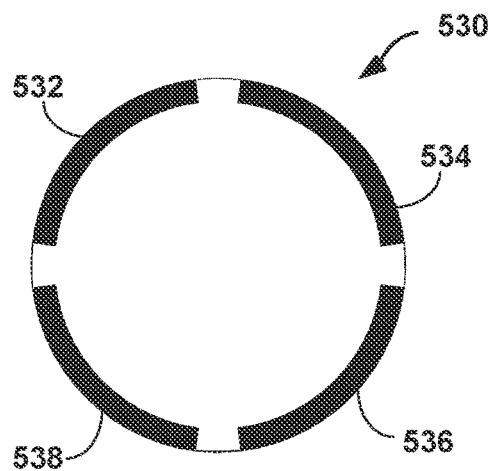
FIG. 5C  FIG. 5D

PROGRAMMING RANK INDEX FOR ELECTRICAL STIMULATION AND RECORDING

TECHNICAL FIELD

This disclosure generally relates to medical devices, and, more specifically, selecting electrodes for electrical stimulation and/or sensing.

BACKGROUND

Medical devices may be external or implanted, and may be used to deliver electrical stimulation therapy to various tissue sites of a patient to treat a variety of symptoms or conditions such as chronic pain, tremor, Parkinson's disease, dystonia, other movement disorders, epilepsy, headache, psychiatric disorders, urinary or fecal incontinence, sexual dysfunction, obesity and eating disorders, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), occipital nerve stimulation (ONS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a waveform pattern, a polarity of each selected electrode, a voltage or current amplitude, a pulse width, and a pulse frequency as stimulation parameters in a multitude of modes continuous/cycling and configurations. A set of parameters which includes voltage or current amplitude, pulse width and pulse rate, in a specific electrode configuration and polarity, may be referred to as a program in the sense that they define the electrical stimulation therapy to be delivered to the patient. Several programs could be assimilated into one or more groups.

SUMMARY

In general, the disclosure describes devices, systems, and techniques for programming and electrode selection for delivery of electrical stimulation. For example, electrodes may be assigned directions corresponding to the direction of the surface of the electrode with respect to anatomy within which the electrode is implanted or the source of a sensed biomarker and may be grouped into sets of electrodes, such as electrode clusters, based on the assigned directions. A subset of electrodes may be identified based on position and direction relative to one or more target regions of tissue and individually ranked based on a ratio of an electrical efficiency or effect threshold to a therapeutic window. The individual rankings may be used to rank the directional sets of electrodes.

A device, programmer, or clinician may select a final electrode set based on a dynamically minimalistic search by providing stimulation with a low number of electrodes in a set of electrodes, observing symptoms, beneficial effects and side-effects, and repeating the stimulation and observation while iteratively adding one or more electrodes until no more reduction in symptoms is observed and/or an undesirable side-effect is induced. Alternatively, a device, programmer, or clinician may select a final electrode set based on a systematically reductive search by providing stimulation with all of the electrodes in a set of electrodes, observing symptoms, beneficial effects and side-effects, and repeating the stimulation and observation while removing one or more electrodes a number of times until side-effects are present and/or symptoms are suppressed. In some examples, a biomarker like the local field potential (LFP) recording or resonant response may be used to supplement the above technique. For example, LFPs may be measured at each electrode to "triangulate" the source (identification and localization) of a biomarker. This source may be compared with the final electrode set. Agreement may add confidence to the identified set but may not change the final electrode set in the event of a disagreement. In some examples, a disagreement between the source and final electrode set may identify an alternative electrode set to the final electrode set determined via stimulation and observation. An example of this scenario would be wherein the selected set of electrodes point in the direction of a sensed biomarker source and the threshold for a therapeutic effect is low along with a narrow therapeutic window (e.g., a small amplitude range between achieving the therapeutic effect and causing an undesirable side effect).

In one example, a system includes processing circuitry configured to: determine, for each respective set of electrodes of a plurality of sets of electrodes, a score based on a ratio of an electrical efficiency for the respective set of electrodes to a therapeutic window for the respective set of electrodes; determine, based on the score of each respective set of electrodes, a ranking of the plurality of sets of electrodes; and select, based on the ranking, a subset of the plurality of sets of electrodes for delivery of electrical stimulation therapy.

In another example, a method includes determining, for each respective set of electrodes of a plurality of sets of electrodes, a score based on a ratio of an electrical efficiency for the respective set of electrodes to a therapeutic window for the respective set of electrodes; determining, based on the score of each respective set of electrodes, a ranking of the plurality of sets of electrodes; and selecting, based on the ranking, a subset of the plurality of sets of electrodes for delivery of electrical stimulation therapy.

In another example, a computer-readable storage medium including instructions that, when executed, cause processing circuitry to determine, for each respective set of electrodes of a plurality of sets of electrodes, a score based on a ratio of an electrical efficiency for the respective set of electrodes to a therapeutic window for the respective set of electrodes; determine, based on the score of each respective set of electrodes, a ranking of the plurality of sets of electrodes; and select, based on the ranking, a subset of the plurality of sets of electrodes for delivery of electrical stimulation therapy.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

FIGS. 4A and 4B are conceptual diagrams of example leads with respective electrodes carried by the lead.

FIGS. 5A, 5B, 5C, 5D, 5E, 5F, and 5G are conceptual diagrams of example electrodes disposed around a perimeter of a lead at a particular longitudinal location.

DETAILED DESCRIPTION

Figure 1:
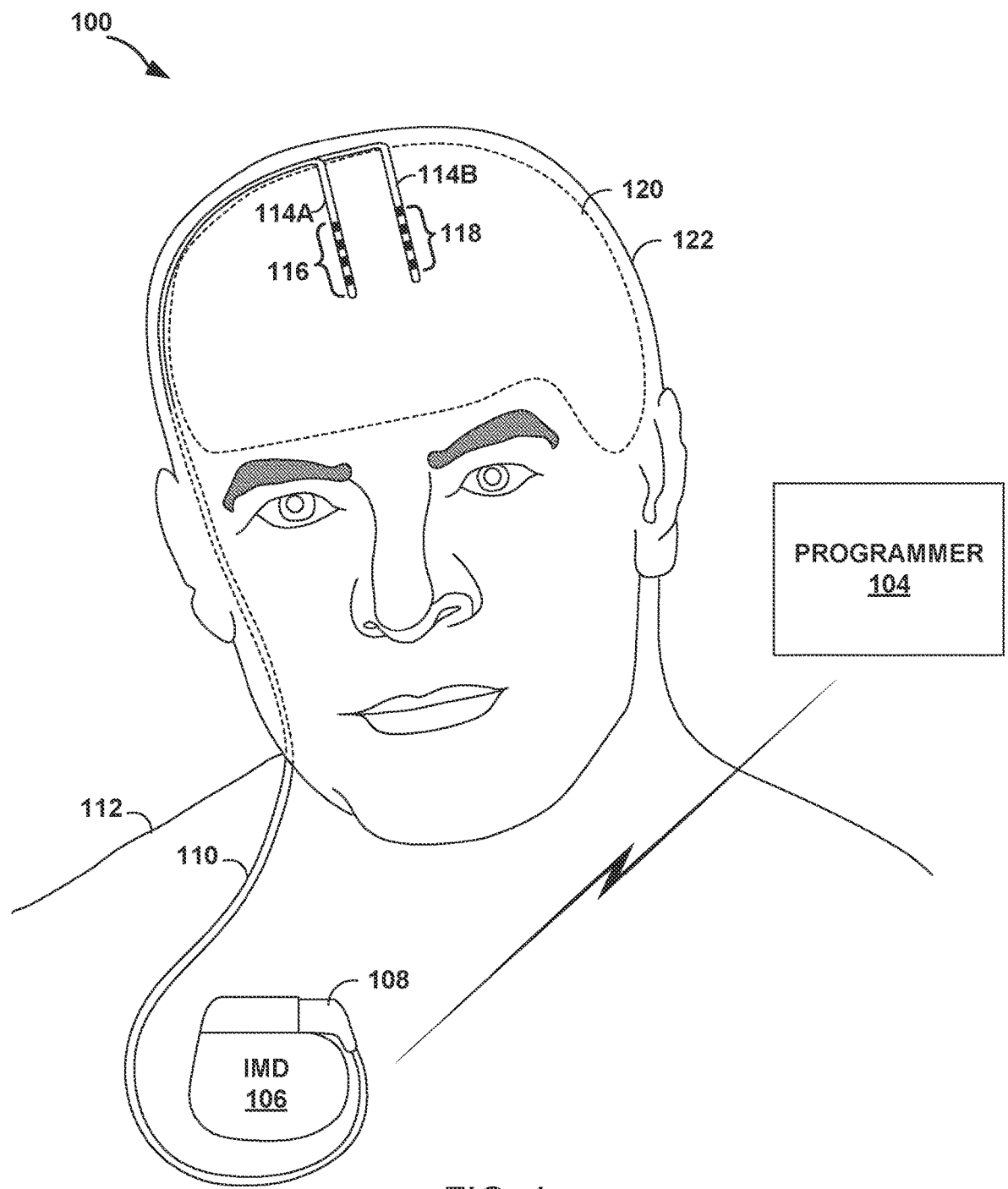
FIG. 1 is a conceptual diagram illustrating an example system that includes an implantable medical device (IMD) configured to deliver DBS to a patient according to an example of the techniques of the disclosure.

This disclosure describes various devices, systems, and techniques for determining electrodes for recording electrical signals and/or delivering electrical stimulation therapy. A patient may suffer from one or more symptoms treatable by electrical stimulation therapy. For example, a patient may suffer from brain disorder such as chronic pain, tremor, Parkinson's disease, dystonia, other movement disorders, epilepsy, headache, psychiatric disorders, urinary or fecal incontinence, sexual dysfunction, obesity and eating disorders, or gastroparesis, other neurological or psychiatric disorder. Deep brain stimulation (DBS) may be an effective treatment to reduce the symptoms associated with such disorders. However, efficacy of stimulation therapy may be reliant on therapy programming, e.g., selecting appropriate individual electrodes and/or sets of electrodes, e.g., such as electrode clusters, and other stimulation parameter values that direct an electric field to a target region (or sub-region) of tissue (e.g. towards the source of a qualified sensed biomarker). Inadequate stimulation of target tissue may not effectively reduce patient symptoms or overstimulation of the target tissue may paradoxically worsen symptoms. Conversely, stimulation of tissue outside of the target region may elicit undesirable side-effects and/or reduce the efficacy of the therapy. Therapy programming may be a time-intensive and iterative process in which a clinician may determine stimulation parameters based on observed reduction in symptoms and/or onset of side-effects over multiple trials and multiple office visits by the patient. The emergence of directional electrodes (e.g., electrodes at different positions around a perimeter, such as a shaft, of a lead), while providing a further degree of freedom to control electrical stimulation by current fractionalization for improved efficacy, electrical efficiency and an enhanced therapeutic window, increases the complexity and time required for programming via increasing the number of variables to be determined during programming.

As described herein, various devices, systems, and techniques may determine a subset of a plurality of electrodes of one or more leads of an IMD based on position and direction relative to one or more target regions of tissue and an electrode rank based on an electrode score indicative of the therapeutic efficacy of each of the electrodes in the subset. In some examples, a system may assign directions to electrodes that correspond to the direction of the surface of the electrode and may group electrodes into sets of electrodes based on the assigned directions, e.g., directional sets of electrodes. For example, the system, a device, a programmer, or a clinician may designate a marking and/or reference electrode for determining the spatial and/or directional orientation of an IMD at the time of IMD implantation or post-operatively, and the system may determine the directions of the rest of the electrodes based on the determined direction of the marking electrode and relative to anatomy within which the electrode is implanted. The system may determine the spatial and/or directional orientation of the IMD based on the marking electrode using intra-operative techniques, e.g., directional acute stimulation and/or imaging techniques such as lateral fluoroscopy, O-Arm, computed tomography (CT), and the like. An implanting team and/or surgeon may determine the spatial and/or directional orientation of the IMD based on the marking electrode using high resolution imaging techniques such as a target-specific conditionally safe magnetic resonance imaging (MRI) sequence which may be used to create a patient specific "atlas." In some examples, the system, a programmer, or a clinician may assign a primary direction, e.g., anterior, posterior, medial, and lateral, and a secondary direction, e.g., anterior-medial, anterior-lateral, posterior-medial and posterior-lateral to each electrode, e.g., based on the determined directional orientation of the marking electrode relative to anatomy within which the marking electrode is implanted and predetermined directional orientations of each electrode relative to the marking electrode.

The system may identify a subset of electrodes based on electrode position and the assigned primary and/or secondary direction relative to one or more target regions of tissue and may individually rank each electrode of the subset of electrodes (or each set of electrodes of the subset of plurality of sets of electrodes) based on a ratio of electrical efficiency to therapeutic window. The system may rank the directional sets of electrodes based on the individual rankings. In some examples, the system may identity sets of electrodes based on individual electrode position and assigned primary and/or secondary directions and rank the sets of electrodes. The system, a device, a programmer, or a clinician may select a final electrode set based on a dynamically minimalistic search by providing stimulation with a low number of electrodes in a set of electrodes, observing symptoms, beneficial effects and side-effects, and repeating the stimulation and observation while adding one or more electrodes a number of times until no more reduction in symptoms is observed, an undesirable side-effect is induced, or a favorable or unfavorable change in a sensed biomarker occurs. Alternatively, the system, a device, a programmer, or a clinician may select a final electrode set based on a systematically reductive search by providing stimulation with all of the electrodes in a set of electrodes, observing symptoms, beneficial effects and side-effects, and repeating the stimulation and observation while removing one or more electrodes a number of times until side-effects are present, symptoms re-appear, or a favorable or unfavorable change in a sensed biomarker occurs. In some examples, LFP recording (or any biomarker or resonant response) may be used to supplement the above technique. For example, the system, a device, a programmer, or a clinician may measure/calculate LFPs at each electrode or set of electrodes to "triangulate" the source of a biomarker. The system may compare the source location with the directionality of the selected electrode set. Agreement may add confidence to the identified set but may not change the final electrode set in the event of a disagreement. In some examples, a disagreement may identify an alternative electrode set to the final electrode set determined via stimulation and observation. In some examples, source locations and directionalities of the selected electrode set may be implemented in a set of programs in another stimulation group of electrodes for evaluation, e.g., by a clinician, patient, or user. In some examples, the selected electrode set may be used for sensing, e.g., to verify changes in sensed signal characteristics after stimulation through the other stimulation group of electrodes.

The devices, systems, and techniques of the present disclosure may reduce the complexity and number of electrodes for programming effective therapy and may reduce programming time and number of patient visits for therapy programming. Moreover, these scoring and ranking techniques may improve electrode selection and provide optimal efficacious therapy with reduced or eliminated undesirable side-effects.

Although this disclosure is directed to DBS therapy, the systems, devices, and techniques described herein may similarly improve therapy programming of leads and electrodes implanted outside of the brain, such as near other nerves or muscles for different diagnostic or therapeutic applications, such as occipital nerve stimulation (ONS), spinal cord stimulation (SCS), pelvic stimulation, sacral nerve stimulation, gastric stimulation, or peripheral nerve field stimulation (PNFS). Moreover, a human patient is described for example purposes herein, but similar systems, devices, and techniques may be used for other animals in other examples.

FIG. 1 is a conceptual diagram illustrating an example system 100 that includes an implantable medical device (IMD) 106 configured to deliver DBS to patient 112 according to an example of the techniques of the disclosure. As shown in the example of FIG. 1, example system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the thalamus, subthalamic nucleus, or globus pallidus may be an effective treatment to manage movement disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver adaptive or closed loop (e.g. triggered by sensed events to reset the cycling) electrical stimulation to brain 120. In other examples, all of electrodes 116, 118 are configured to both sense neurological brain signals and deliver adaptive electrical stimulation to brain 120.

IMD 106 includes a therapy module (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the configuration and/or polarity of the subset of electrodes 116, 118, may be referred to as a stimulation electrode combination. As described in further detail below, the stimulation electrode combination can be selected for a particular patient 112 and target tissue site (e.g., selected based on the patient specific conditions like disease, symptoms, brain state etc.). The group of electrodes 116, 118 includes at least one electrode and can include a plurality of electrodes. In some examples, the plurality of electrodes 116 and/or 118 may have a complex electrode geometry such that two or more electrodes of the lead are located at different positions around the perimeter of the respective lead (e.g., different positions around a longitudinal axis of the lead).

In some examples, electrical signals, such as neurological brain signals, sensed within brain 120 may reflect changes in electrical current produced by the sum and/or summation of electrical potential differences across brain tissue. Examples of neurological brain signals include, but are not limited to, electrical signals generated from LFPs sensed within one or more regions of brain 120, or an evoked resonant response or an electroencephalogram (EEG) signal, or an electrocorticogram (ECoG) signal. The sensed signal, however, may include a broader genus of electrical signals within brain 120 of patient 112.

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, due to these differences in target locations, in some examples, the electrodes used for delivering electrical stimulation may be different than the electrodes used for sensing neurological brain signals. In other examples, the same electrodes may be used to both deliver electrical stimulation and sense brain signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave, triangle wave or other standard/novel charge balanced waveforms. In either case, a stimulation generator within IMD 106 may generate the electrical stimulation therapy for DBS according to a therapy program that is selected at that given time in therapy. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes. IMD 106 may deliver electrical stimulation intended to contribute to a therapeutic effect. In some examples, IMD 106 may also, or alternatively, deliver a conditioning sub-threshold pre-pulse immediately prior to the stimulation pulse or electrical stimulation intended to be sensed by other electrodes and/or elicit a physiological response, such as an evoked compound action potential (ECAP) or resonant response, that can be sensed by electrodes.

IMD 106 may be implanted within a subcutaneous pocket below the clavicle, or, in the abdomen or alternatively, on or within cranium 122 or at any other suitable site within patient 112. Generally, IMD 106 is constructed of a biocompatible material that resists corrosion and degradation from body fluids. IMD 106 may comprise a hermetic housing to substantially enclose components, such as a processor, therapy module, and memory. In some examples, IMD 106 may be a primary cell IMD. In other examples, IMD 106 may be a rechargeable IMD, e.g., including rechargeable batteries.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres, respectively, of patient 112 in order deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to patient behaviors, e.g., as patient behaviors associated with one or more brain disorders, and/or other sensed patient signals. Other lead 114 and IMD 106 implant sites are contemplated. For example, IMD 106 may be implanted on or within cranium 122, in some examples. Or leads 114 may be implanted within the same hemisphere or IMD 106 may be coupled to a single lead implanted in a single hemisphere. Although leads 114 may have ring (annular having cylindric symmetric design) electrodes at different longitudinal positions as shown in FIG. 1, leads 114 may have electrodes disposed at different positions around the perimeter of the lead (e.g., different circumferential positions for a cylindrical shaped lead) as shown in the examples of FIGS. 5B-5G.

Leads 114 illustrate an example lead set that include axial leads carrying ring electrodes disposed at different axial positions (or longitudinal positions). In other examples, leads may be referred to as "paddle" leads carrying planar arrays of electrodes on one side of the lead structure. In addition, as described herein, complex lead array geometries may be used in which electrodes are disposed at different respective longitudinal positions and different positions around the perimeter of the lead. As described herein, IMD 106 may be configured to select and/or receive a selection of a subset of electrodes based on an electrical efficiency and a therapeutic window of electrical stimulation delivered by the subset of electrodes.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms of patient 112. Leads 114 may be implanted to position electrodes 116, 118 at desired locations of brain 120 through respective burr holes in cranium 122. Leads 114 may be placed at any location within brain 120 such that electrodes 116, 118 are capable of recording/sensing signals from or providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring (omnidirectional) electrodes may be used in DBS applications because they are relatively less complex to program and are capable of delivering an electrical field to any tissue adjacent to electrodes 116, 118. In other examples, electrodes 116, 118 may have different geometric designs. For example, in some examples, at least some of the electrodes 116, 118 of leads 114 may have a complex electrode array geometry that is capable of producing shaped electrical fields to steer the fractionalized energy. The complex electrode array geometry may include multiple electrodes (e.g., partial ring or segmented electrodes) around the outer perimeter of each lead 114, rather than one ring electrode, such as shown in FIGS. 4A and 4B. In this manner, fractionalized electrical stimulation may be directed in a specific direction from leads 114 to enhance therapy efficacy and reduce possible adverse side-effects from stimulating a large volume of tissue. In some examples, a housing of IMD 106 may include one or more stimulation and/or sensing electrodes. In alternative examples, leads 114 may have shapes other than elongated cylinders as shown in FIG. 1. For example, leads 114 may have active/passive distal tips or be paddle leads, spherical leads, bendable leads, or any other type of shape effective in treating patient 112 and/or minimizing invasiveness of leads 114.

In the example shown in FIG. 1, IMD 106 includes a memory to store a plurality of therapy programs that each define a set of therapy parameter values. In some examples, IMD 106 may select a therapy program from the memory based on various criteria, such as sensed patient signals and the identified patient behaviors. In some examples, the sensed patient signals may contain event tags that correlate with the occurrence of a qualified biomarker representing a specific symptom/brain/disease state. IMD 106 may generate electrical stimulation based on the selected therapy program to manage the patient symptoms.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs/groups for IMD 106. Alternatively, programmer 104 may be a patient programmer that allows patient 112 to switch the therapy on/off, check IMD battery status, select programs/groups and/or view and modify therapy parameters (limits of which may be set by the clinician programmer), trigger sensing and enter events to synchronize with concomitant sensing for tagging recorded signals. The clinician programmer may include more programming features than the patient programmer. In other words, more complex or sensitive tasks may only be allowed by the clinician programmer to prevent an untrained patient from making undesirable changes to IMD 106. Programmer 104 may enter a new programming session for the user to select new stimulation parameters for subsequent therapy.

When programmer 104 is configured for use by the clinician, programmer 104 may be used to transmit (or query) initial programming information to IMD 106. This initial information may include hardware information, such as the type of leads 114 and the electrode arrangement, the location of leads 114 within brain 120, the direction of one or more of electrodes 116, 118, the configuration of electrode array 116, 118, initial programs defining therapy parameter values, and any other information the clinician desires to program into IMD 106. Programmer 104 may also be capable of completing functional tests (e.g., measuring the electrode/therapy impedance of electrodes 116, 118 of leads 114). The clinician programmer may be able to display the live streaming data or recorded/sensed signals with/ without event tags in a plurality of formats or perform an analysis on the acquired data for e.g. to identify signal characteristics.

The clinician may also store therapy programs within IMD 106 with the aid of programmer 104. During a programming session, the clinician may determine one or more therapy programs that may provide efficacious therapy to patient 112 to address symptoms associated with the disease condition, and, in some cases, specific to one or more different patient states, such as a sleep state, movement state, rest state or individual disease or symptom state. For example, the clinician may select one or more stimulation electrode combination with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). Sometimes recorded or sensed signals from leads 114 obtained at different instances in time (e.g. prior to stimulation and after stimulation or after stimulation with temporal precedence depending on the latency of response, resonant response) may also provide insights into efficacy of the specific program being evaluated. Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter or select between programmed therapy groups which have been pre-assigned by the clinician or trigger a cycling reset or initiate sensing capture triggered by a patient event.

Programmer 104 may also provide an indication to patient 112 when therapy is being delivered, when patient input has triggered a change in therapy or when the power source within programmer 104 or IMD 106 needs to be replaced (e.g., low power, elective replacement indicator, end of service etc.) or recharged. For example, programmer 112 may include an alert LED, may flash a message to patient 112 via a programmer display, generate an audible sound or somatosensory cue to confirm patient input was received, e.g., to indicate a patient state or to manually modify a therapy parameter. Programmer 104 may also be configured to initiate sensing/recording (with or without event markers) from clinician programmed electrodes in varying lengths of time for capturing stochastic events or tag events alongside sensing data to provide markers for the clinician to analyze with time or event stamps.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator (e.g. an external neurostimulator), rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112 in other examples. In other examples, system 100 may include an implantable drug pump in addition to, or in place of, IMD 106. Further, an IMD may provide other electrical stimulation such as spinal cord stimulation to treat a movement disorder.

According to the techniques of the disclosure, system 100 and/or a clinician or user of system 100 may determine a subset of a plurality of electrodes of one or more leads of IMD 106 to deliver electrical stimulation therapy. For example, system 100 may determine the subset of electrodes (e.g., an electrode combination) based on a position and a direction relative to one or more target regions of tissue and an electrode rank based on an electrode score indicative of the therapeutic efficacy of each of the electrodes in the subset. For example, a clinician and/or user may specify a marking electrode from a plurality of electrodes of lead 114A and/or 114B. In some examples, the clinician and/or user may specify the marking electrode based on a directional marker for ascertaining spatial orientation at the time of lead implantation, e.g., a radiopaque stripe, a tab, detent, or other structure on the outside of lead 114A and/or 114B housing.

Figure 2:
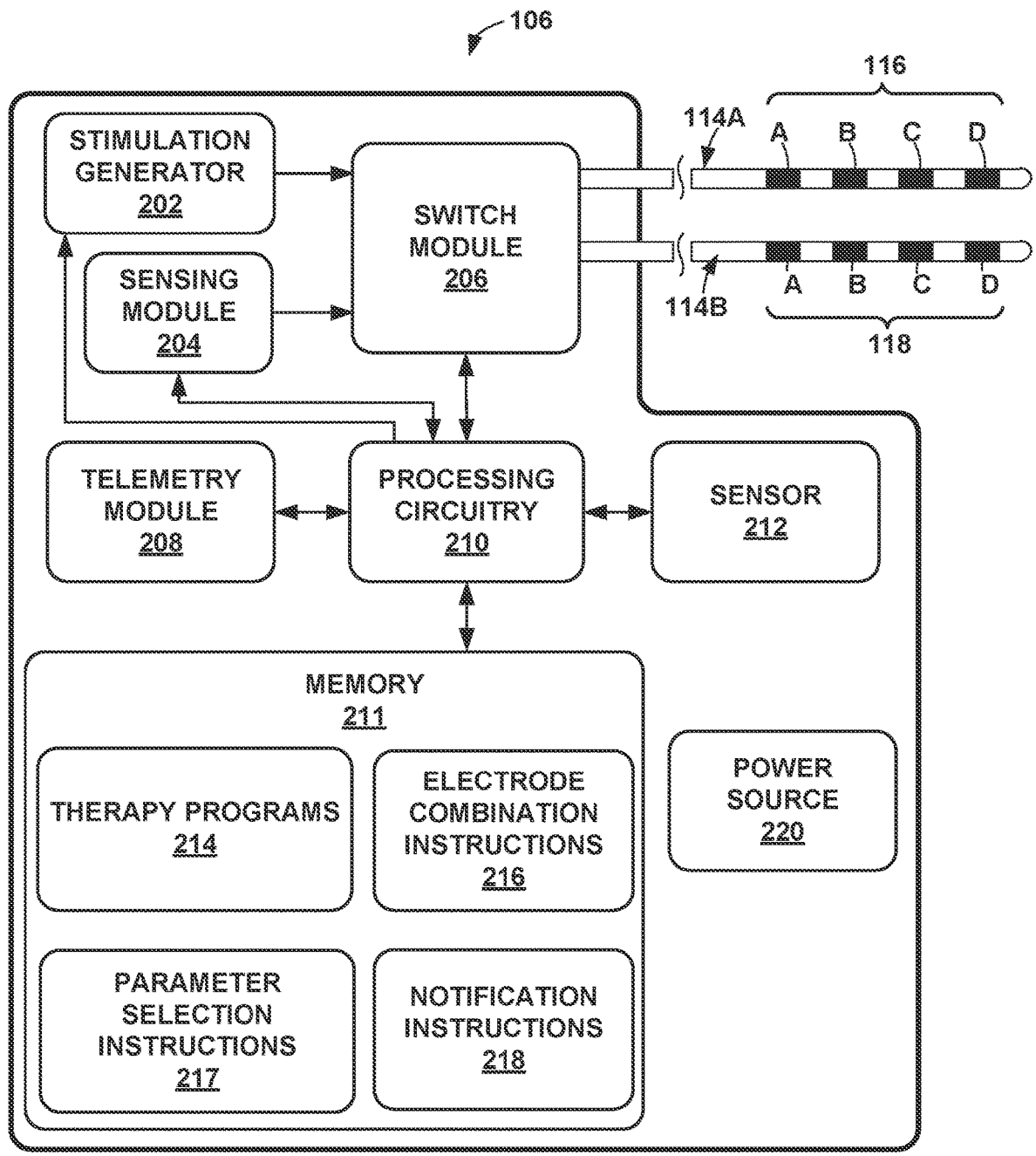
FIG. 2 is a block diagram of the example IMD of FIG. 1 for delivering DBS therapy according to an example of the techniques of the disclosure.

A device, programmer 104, IMD 106, clinician and/or processing circuitry 210 (as shown in FIG. 2) may assign a primary direction and one or more secondary directions to each of the electrodes of each of the leads based on the marking electrode and reference direction relative to anatomy within which the electrodes are implanted. For example, system 100 (e.g., IMD 106 and/or programmer 104) may also include processing circuitry configured to assign a primary direction and one or more secondary directions to each of the electrodes relative to anatomy within which the electrode is implanted, and/or system 100 may allow a clinician and/or user to manually select electrode primary and secondary directions and/or override the selections made by processing circuitry. The device, programmer 104, IMD 106, clinician and/or processing circuitry 210 may determine a subset of electrodes to be ranked for programming that is less than the plurality of electrodes of the lead(s) and may exclude the remaining electrodes from ranking and programming. For example, programmer 104 may determine the subset of electrodes based on assigned direction and/or location of each respective electrode relative to a target region of tissue or presence or absence of a qualified biomarker or resonant response, which may reduce the complexity of programming by reducing the number of electrodes and/or electrode combinations to evaluate for therapy optimization. The device, programmer 104, IMD 106, clinician and/or processing circuitry 210 may determine a stimulation ranking of the electrodes of the subset of electrodes, e.g., based on a multiple criteria optimization scheme, as further illustrated and described below with reference to FIG. 8. For example, programmer 104 may determine the stimulation ranking via determining an electrode score based on an inferred electrical efficiency and therapeutic window for each monopolar configuration of electrodes based on physiological effects, e.g., an alleviation of symptoms as assessed by a clinician and/or neurologist and, in some example, with insight from sensed/recorded signals which may contain a qualified biomarker or resonant response indicating disease/brain/symptom state. The device, programmer 104, IMD 106, clinician and/or processing circuitry 210 may assign a locus electrode for one or more of the primary and secondary directions and may determine a stimulation electrode combination for programming based on physiological effects and via one or more search schemes, as further illustrated and described below with reference to FIG. 8. For example, the locus electrode may be the closest electrode to one or more target regions of tissue (based on patient specific anatomy or identified by source localization of a sensed biomarker) and may have a directional orientation suitable for effectively delivering stimulation to one or more target regions of tissue, e.g., efficiently and with a relatively wide therapeutic window. The locus electrode may serve as a reference basis for adding or removing other electrodes from delivering stimulation, e.g., based on their spatial proximity to the locus electrode and/or being assigned the same primary and/or secondary directions as the locus electrode. For example, if larger stimulation field/volume would deliver a better efficacious therapy, electrodes near the locus electrode and facing substantially the same direction may be used in addition to the locus electrode (or one or more or all of their parameters may be augmented selectively), e.g., added to a subset of electrodes programmed to deliver a greater electrical stimulation therapy dose. Conversely, if lesser stimulation would deliver efficacious therapy while reducing one or more side-effects, electrodes farthest away from the locus electrode and/or facing in a direction that differs from the locus electrode (more than other electrodes) may be excluded from delivering therapy (or one or more or all of their parameters could be reduced selectively), e.g., excluded from the subset of electrodes programmed to deliver a reduced electrical stimulation therapy dose by reducing electrical stimulation in areas and or directions that may be less efficient relative to other electrodes in the subset programmed to deliver the therapy. The architecture of system 100 illustrated in FIG. 1 is shown as an example. The techniques as set forth in this disclosure may be implemented in the example system 100 of FIG. 1, as well as other types of systems not described specifically herein. Nothing in this disclosure should be construed so as to limit the techniques of this disclosure to the example architecture illustrated by FIG. 1.

FIG. 2 is a block diagram of the example IMD 106 of FIG. 1 for delivering DBS therapy. In the example shown in FIG. 2, IMD 106 includes processing circuitry 210, memory 211, stimulation generator 202, sensing module 204, switch module 206, telemetry module 208, sensor 212, and power source 220. Each of these modules may be or include electrical circuitry configured to perform the functions attributed to each respective module. For example, processing circuitry 210 may include processing circuitry, switch module 206 may include switch circuitry, sensing module 204 may include sensing circuitry, and telemetry module 208 may include telemetry circuitry. Switch module 204 may not be necessary for multiple current source and sink configurations and/or in instances wherein dedicated sensing and stimulation electrode sets are used. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processing circuitry 210, cause IMD 106 to perform various functions. Memory 211 may be a storage device or other non-transitory medium.

In the example shown in FIG. 2, memory 211 stores therapy programs 214 that include respective stimulation parameter sets that define therapy. Each stored therapy program 214 defines a particular set of electrical stimulation parameters (e.g., a therapy parameter set), such as a stimulation electrode configuration and combination, electrode polarity, waveform pattern, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Memory 211 may also include electrode combination instructions 216 that define the process by which processing circuitry 210 determines a stimulation electrode combination for programming. Electrode combination instructions 216 may also include instructions that define the frequency with which processing circuitry 210 controls sensing electrical signals and determining one or more characteristics of the electrical signals that are used to monitor if stimulation electrode combinations change. Memory 211 may also include parameter selection instructions 217 and notification instructions 218. Parameter selection instructions 217 may include instructions that control processing circuitry 210 selecting different stimulation parameter values such as waveform patterns, amplitudes, pulse frequencies, pulse widths, or other parameter values for delivering electrical stimulation. Notification instructions 218 may define instructions that control processing circuitry 210 actions such as transmitting an alert or other notification to an external device, such as programmer 104. In some examples, notification instructions 218 may also define additional information that processing circuitry 210 transmits with the alert, such as any qualified event detected and/or sensed by sensing module 204 such as an LFP signal, or any other information that may assist the user in selecting new stimulation parameters.

In some examples, the sense and stimulation electrode combinations may include the same subset of electrodes 116, 118, a housing of IMD 106 functioning as an electrode, or may include different subsets or combinations of such electrodes. Thus, memory 211 can store a plurality of sense electrode combinations and, for each sense electrode combination, store information identifying the stimulation electrode combination that is associated with the respective sense electrode combination or vice versa. The associations between sense and stimulation electrode combinations can be determined, e.g., by a clinician or automatically by processing circuitry 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In other examples, a sense electrode combination may include more electrodes than the corresponding stimulation electrode combination to increase the accuracy of determining a biomarker source. In some examples, as discussed above, stimulation may be delivered via a stimulation electrode combination to a tissue site that is different than the tissue site closest (e.g. a biomarker source) to the corresponding sense electrode combination but is within the same region, e.g., the thalamus, of brain 120 in order to mitigate any irregular oscillations or other irregular/abnormal brain activity within the tissue site associated with the sense electrode combination. In other examples, stimulation may be delivered via a stimulation electrode combination to a tissue site that is different from the location of the sense electrode combination (e.g. stimulation electrode set in the subthalamic nucleus and the sense electrode set in the substantia nigra to record the resonant response).

Stimulation generator 202, under the control of processing circuitry 210, generates stimulation signals for delivery to patient 112 via selected combinations of electrodes 116, 118. An example range of electrical stimulation parameters in a plurality of waveform patterns believed to be effective in DBS to manage a movement disorder of patient include:
1. Pulse Rate, i.e., Frequency: between approximately 40 Hertz and approximately 500 Hertz, such as between approximately 40 to 185 Hertz or such as approximately 140 Hertz.
2. In the case of a voltage-controlled system, Voltage Amplitude: between approximately 0.1 volts and approximately 50 volts, such as between approximately 2 volts and approximately 3 volts.
3. In the alternative case of a current-controlled system, Current Amplitude: between approximately 0.2 milliamps to approximately 100 milliamps, such as between approximately 1.3 milliamps and approximately 2.0 milliamps.
4. Pulse Width: between approximately 10 microseconds and approximately 5000 microseconds, such as between approximately 100 microseconds and approximately 1000 microseconds, or between approximately 30 microseconds and approximately 450 microseconds.

Accordingly, in some examples, stimulation generator 202 generates electrical stimulation signals in accordance with the electrical stimulation parameters noted above. Other ranges of therapy parameter values may also be useful and may depend on the target stimulation site within patient 112. While stimulation pulses are described, stimulation signals may be of any form, such as continuous-time signals (e.g., sine waves) or the like. Stimulation signals configured to elicit ECAPs or other evoked physiological signals may be similar or different from the above parameter value ranges.

Processing circuitry 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 may control stimulation generator 202 according to therapy programs 214 stored in memory 211 to apply particular stimulation parameter values specified by one or more of programs, such as waveform pattern, voltage amplitude or current amplitude, pulse width, or pulse rate.

In the example shown in FIG. 2, the set of electrodes 116 includes electrodes 116A, 116B, 116C, and 116D, and the set of electrodes 118 includes electrodes 118A, 118B, 118C, and 118D. Processing circuitry 210 also controls switch module 206 to apply the stimulation signals generated by stimulation generator 202 to selected combinations of electrodes 116, 118. In particular, switch module 206 may couple stimulation signals to selected conductors within leads 114, which, in turn, deliver the stimulation signals across selected electrodes 116, 118. Switch module 206 may be a switch array, switch matrix, multiplexer, or any other type of switching module configured to selectively couple stimulation energy to selected electrodes 116, 118 and to selectively sense neurological brain signals with selected electrodes 116, 118. Hence, stimulation generator 202 is coupled to electrodes 116, 118 via switch module 206 and conductors within leads 114. In some examples, however, IMD 106 does not include switch module 206.

Stimulation generator 202 may be a single channel or multi-channel stimulation generator. In particular, stimulation generator 202 may be capable of delivering a single stimulation pulse, multiple stimulation pulses, or a continuous signal at a given time via a single electrode combination or multiple stimulation pulses at a given time via multiple electrode combinations. In some examples, however, stimulation generator 202 and switch module 206 may be configured to deliver multiple channels on a time-interleaved basis. For example, switch module 206 may serve to time divide the output of stimulation generator 202 across different electrode combinations at different times to deliver multiple programs or channels of stimulation energy to patient 112. Alternatively, stimulation generator 202 may comprise multiple voltage or current sources and sinks that are coupled to respective electrodes to drive the electrodes as cathodes or anodes. In this example, IMD 106 may not require the functionality of switch module 206 for time-interleaved multiplexing of stimulation via different electrodes.

Electrodes 116, 118 on respective leads 114 may be constructed of a variety of different designs. For example, one or both of leads 114 may include two or more electrodes at each longitudinal location along the length of the lead, such as multiple electrodes at different perimeter locations around the perimeter of the lead at each of the locations A, B, C, and D. In one example, the electrodes may be electrically coupled to switch module 206 via respective wires that are straight or coiled within the lead housing and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 114. These and other constructions may be used to create a lead with a complex electrode geometry.

Although sensing module 204 is incorporated into a common housing with stimulation generator 202 and processing circuitry 210 in FIG. 2, in other examples, sensing module 204 may be in a separate housing from IMD 106 and may communicate with processing circuitry 210 via wired or wireless communication techniques. Example neurological brain signals sensed include, but are not limited to, a signal generated from LFPs within one or more regions of brain 120. EEG and ECoG are examples of sensed signals that may be measured within brain 120. However, sensed signal may include a broader genus of electrical signals within brain 120 of patient 112.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 106 may include additional sensors within the housing of IMD 106 and/or coupled via one of leads 114 or other leads. In addition, IMD 106 may receive sensor signals wirelessly from remote sensors via telemetry module 208, for example. In some examples, one or more of these remote sensors may be external to patient (e.g., carried on the external surface of the skin, attached to clothing, a wearable sensor, or otherwise positioned external to the patient).

Telemetry module 208 supports wireless communication between IMD 106 and an external programmer 104 or another computing device under the control of processing circuitry 210. Processing circuitry 210 of IMD 106 may receive, as updates to programs, values for various stimulation parameters such as magnitude and electrode combination, from programmer 104 via telemetry module 208. The updates to the therapy programs may be stored within therapy programs 214 portion of memory 211. In addition, processing circuitry 210 may control telemetry module 208 to transmit alerts which may be based on but not limited to sensed data or other information to programmer 104 relating to determination of a stimulation electrode combination for programming. Telemetry module 208 in IMD 106, as well as telemetry modules in other devices and systems described herein, such as programmer 104, may accomplish communication by radiofrequency (RF) communication techniques. In addition, telemetry module 208 may communicate with external medical device programmer 104 via proximal inductive interaction of IMD 106 with programmer 104. Accordingly, telemetry module 208 may send information to external programmer 104 on a continuous basis, at periodic intervals, triggered by sensed events, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within power source 220. In some examples, power requirements may be small enough to allow power source 220 to utilize patient motion and implement a kinetic energy-scavenging device to trickle charge a rechargeable battery. In other examples, traditional batteries may be used for a limited period of time.

According to the techniques of the disclosure, processing circuitry 210 of IMD 106 delivers, via electrodes 116, 118 interposed along leads 114 (and optionally switch module 206), electrical stimulation therapy to patient 112. The DBS therapy is defined by one or more therapy programs 214 having one or more parameters stored within memory 211. For example, the one or more parameters may include a waveform pattern, a current amplitude (for a current-controlled system) or a voltage amplitude (for a voltage-controlled system), a pulse rate or frequency, and a pulse width, or quantity of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time.

In some examples, sensing module 204 may sense an electrical signal that is a neurological signal (e.g., an LFP signal) within the beta (13-30 Hz) frequency band (or any other relevant band or bands in a sensed biomarker) of brain 120 of patient 112. The signal within the LFP beta frequency band of patient 112 may correlate to one or more symptoms of Parkinson's disease in patient 112. Generally speaking, neurological signals within the LFP beta frequency band of patient 112 may be approximately proportional to the severity of the symptoms or a disease state (e.g. on medications or off medications) of patient 112. For example, as bradykinesia/rigidity induced by Parkinson's disease increases, one or more of electrodes 116, 118 detect an increase in the magnitude of neurological signals within the LFP beta frequency band of patient 112. In this manner, the closest electrode combination to the origin/source of this neurological signal may be selected for therapy. In other instances, the closest electrode combination to the origin/source of the sensed signal may be avoided for therapy.

Figure 3:
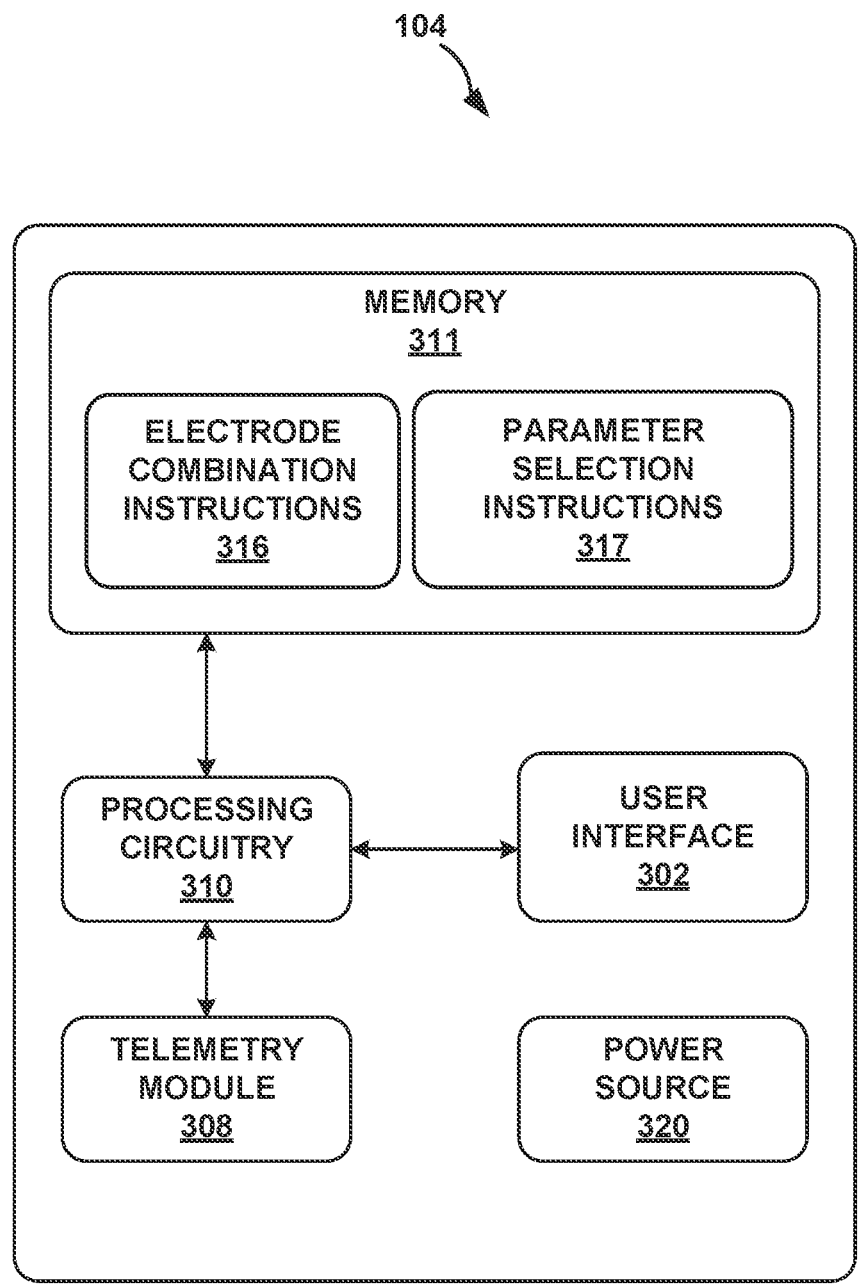
FIG. 3 is a block diagram of the external programmer of FIG. 1 for controlling delivery of DBS therapy according to an example of the techniques of the disclosure.

FIG. 3 is a block diagram of the external programmer 104 of FIG. 1 for controlling delivery of DBS therapy according to an example of the techniques of the disclosure. Although programmer 104 may generally be described as a hand-held device, programmer 104 may be a larger portable device or a more stationary device. In some examples, programmer 104 may be referred to as a tablet computing device. In addition, in other examples, programmer 104 may be included as part of an external charging device or include the functionality of an external charging device. As illustrated in FIG. 3, programmer 104 may include a processing circuitry 310, memory 311, user interface 302, telemetry module 308, and power source 320. Each of these components, or modules, may include electrical circuitry that is configured to perform some, or all of the functionality described herein. For example, processing circuitry 310 may include processing circuitry configured to perform the processes discussed with respect to processing circuitry 310. Memory 311 may store instructions that, when executed by processing circuitry 310, cause processing circuitry 310 and external programmer 104 to provide the functionality ascribed to external programmer 104 throughout this disclosure.

In general, programmer 104 comprises any suitable arrangement of hardware, alone or in combination with software and/or firmware, to perform the techniques attributed to programmer 104, and processing circuitry 310, user interface 302, and telemetry module 308 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, a DVD, comprising executable instructions for causing the one or more processors to perform the actions attributed to them. Moreover, although processing circuitry 310 and telemetry module 308 are described as separate modules, in some examples, processing circuitry 310 and telemetry module 308 may be functionally integrated with one another. In some examples, processing circuitry 310 and telemetry module 308 correspond to individual hardware units, such as ASICs, DSPs, FPGAs, or other hardware units.

Memory 311 (e.g., a storage device) may store instructions that, when executed by processing circuitry 310, cause processing circuitry 310 and programmer 104 to provide the functionality ascribed to programmer 104 throughout this disclosure. For example, memory 311 may include instructions that cause processing circuitry 310 to obtain a parameter set from memory, provide an interface that recommends or otherwise facilitates parameter value selection, or receive a user input and send a corresponding command to IMD 106, or instructions for any other functionality. In addition, memory 311 may include a plurality of programs, where each program includes a parameter set that defines stimulation therapy.

Memory 311 may store therapy programs that include respective stimulation parameter sets that define therapy, e.g., that may be sent to IMD 106 and may be copies of, or in addition to, therapy programs stored by memory 211. As described above with respect to stored therapy programs 214, each therapy program stored by memory 311 may define a particular set of electrical stimulation parameters (e.g., a therapy parameter set), such as a waveform pattern, stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Memory 311 may also include electrode combination instructions 316 that define the process by which processing circuitry 310 determines a stimulation electrode combination for programming. Electrode combination instructions 316 may also include instructions that define the frequency with which processing circuitry 310 controls sensing electrical signals and determining one or more characteristics of the electrical signals that are used to monitor if stimulation electrode combinations change. Memory 311 may also include parameter selection instructions 317. Parameter selection instructions 317 may include instructions that control processing circuitry 310 selecting different stimulation parameter values such as waveform patterns, amplitudes, pulse frequencies, or other parameter values for delivering electrical stimulation.

In some examples, memory 311 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processing circuitry 310. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 120 in order to mitigate any irregular oscillations or other irregular brain activity within/relative to the tissue site associated with the sense electrode combination. In other examples, stimulation may be delivered via a stimulation electrode combination to a tissue site that is different from the location of the sense electrode combination (e.g. stimulation electrode set in the subthalamic nucleus and the sense electrode set in the substantia nigra to record the resonant response).

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient signals with or without event markers (automatically tagged or entered when triggered by the patient), patient behavior criteria, or any other such information. User interface 302 may also receive user input via user interface 302. The input may be, for example, in the form of pressing a button on a keypad or selecting an icon from a touch screen.

Telemetry module 308 may support wireless communication between IMD 106 and programmer 104 under the control of processing circuitry 310. Telemetry module 308 may also be configured to communicate with another computing device via wireless communication techniques, or direct communication through a wired connection. In some examples, telemetry module 308 provides wireless communication via an RF or proximal inductive medium. In some examples, telemetry module 308 includes an antenna, which may take on a variety of forms, such as an internal or external antenna.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection. In some examples, programmer 104 and/or IMD 106 may be configured to encrypt and/or decrypt at least a portion of data being communicated, e.g., to allow a connection to be established without the connection needing to be a secure wireless connection but to also maintain the security of the data being communicated. As described herein, telemetry module 308 may be configured to transmit a spatial electrode movement pattern or other stimulation parameter values to IMD 106 for delivery of stimulation therapy.

According to the techniques of the disclosure, in some examples, processing circuitry 310 of external programmer 104 defines the parameters of a homeostatic therapeutic window, stored in memory 311, for delivering DBS to patient 112. In one example, processing circuitry 310 of external programmer 104, via telemetry module 308, issues commands to IMD 106 causing IMD 106 to deliver electrical stimulation therapy via electrodes 116, 118 of leads 114.

FIGS. 4A and 4B are conceptual diagrams of example leads 400 and 410, respectively, with respective electrodes carried by the lead. As shown in FIGS. 4A and 4B, leads 400 and 410 are examples of leads 114 shown in FIG. 1. As shown in FIG. 4A, lead 400 includes four electrode levels 404 (includes levels 404A-404D) mounted at various lengths of lead housing 402. Lead 400 is inserted into the cranium 122 to a target position within brain 120.

Lead 400 is implanted within brain 120 at a location determined by the clinician to be near an anatomical region to be stimulated. Electrode levels 404A, 404B, 404C, and 404D are equally spaced along the axial length (shaft) of lead housing 402 at different axial positions. Each electrode level 404 may have one, two, three, or more electrodes located at different angular positions around the circumference (e.g., around the perimeter) of lead housing 402. As shown in FIG. 4A, electrode level 404A and 404D include a single respective ring electrode, and electrode levels 404B and 404C each include three electrodes at different circumferential positions. This electrode pattern may be referred to as a 1-3-3-1 lead in reference to the number of electrodes from the proximal end to the distal end of lead 400. Electrodes of one circumferential location may be lined up on an axis parallel to the longitudinal axis of lead 400. Alternatively, electrodes of different electrode levels may be staggered around the circumference of lead housing 402. In addition, lead 400 or 410 may include asymmetrical electrode locations around the circumference, or perimeter, of each lead or electrodes of the same level that have different sizes. These electrodes may include semi-circular electrodes that may or may not be circumferentially aligned between electrode levels.

Lead housing 402 may include a directional marker. In some examples, lead housing 402 may include a radiopaque stripe (not shown) along the outside of the lead housing. The radiopaque stripe corresponds to a certain circumferential electrode (404B and 404C) orientation that allows lead 400 to the imaged when implanted in patient 112. Using the images of patient 112, the clinician can use the radiopaque stripe as a marker for the exact orientation of lead 400 within the brain of patient 112. Alternately the processing circuitry 310 of programmer 104 can also identify the directional marker. Orientation of lead 400 may improve programming of the stimulation parameters by generating the correct electrode configuration to match the stimulation field defined by the clinician. In other examples, a marking mechanism other than a radiopaque stripe may be used to identify the orientation of lead 400. These marking mechanisms may include something similar to a tab, detent, or other structure on the outside of lead housing 402. In some examples, the clinician may note the position of markings along a lead wire during implantation to determine the orientation of lead 400 within patient 112. In some examples, an electrode, e.g., a marking electrode, may be used as a directional marker. In other examples sensed signal source could also be used as a reference to determine a directional marker.

FIG. 4B illustrates lead 410 that includes multiple electrodes at different respective circumferential positions at each of levels 414A-414D. Similar to lead 400, lead 410 is inserted through a burr hole in cranium 122 to a target location within brain 120. Lead 410 includes lead housing 412. Four electrode levels 414 (414A-414D) are located at the distal end of lead 410. Each electrode level 414 is evenly spaced from the adjacent electrode level and includes two or more electrodes. In one example, each electrode level 414 includes three, four, or more electrodes distributed around the circumference of lead housing 412. Therefore, lead 410 includes 414 electrodes in a preferred example. Each electrode may be substantially rectangular in shape. Alternatively, the individual electrodes may have alternative shapes, e.g., circular, oval, triangular, rounded rectangles, or the like.

In alternative examples, electrode levels 404 or 414 are not evenly spaced along the longitudinal axis of the respective leads 400 and 410. For example, electrode levels 404C and 404D may be spaced approximately 3 millimeters (mm) apart while electrodes 404A and 404B are 10 mm apart. Variable spaced electrode levels may be useful in reaching target anatomical regions deep within brain 120 while avoiding potentially undesirable anatomical regions. Variable spaced electrode levels could also be useful in sensing and stimulating different anatomical structures. Further, the electrodes at adjacent levels need not be aligned in the direction as the longitudinal axis of the lead, and instead may be oriented diagonally or any other orientation with respect to the longitudinal axis.

Leads 400 and 410 are substantially rigid to prevent the implanted lead from varying from the expected lead shape. Leads 400 or 410 may be substantially cylindrical in shape. In other examples, leads 400 or 410 may be shaped differently than a cylinder. For example, the leads may include one or more curves to reach target anatomical regions of brain 120. In some examples, leads 400 or 410 may be similar to a flat paddle lead or a conformable lead shaped for patient 112. Also, in other examples, leads 400 and 410 may be of any variety of different polygonal cross sections (e.g., triangle, square, rectangle, octagonal, etc.) taken transverse to the longitudinal axis of the lead.

As shown in the example of passive tip lead 400, the plurality of electrodes of lead 400 includes a first set of three electrodes disposed at different respective positions around the longitudinal axis of the lead and at a first longitudinal position along the lead (e.g., electrode level 404B), a second set of three electrodes disposed at a second longitudinal position along the lead different than the first longitudinal position (e.g., electrode level 404C), and at least one ring electrode disposed at a third longitudinal position along the lead different than the first longitudinal position and the second longitudinal position (e.g., electrode level 404A and/or electrode level 404D). In some examples, electrode level 404D may be a bullet/active tip or cone shaped electrode that covers the distal end of lead 400.

FIGS. 5A-5F are transverse cross-sections of example leads having one or more electrodes around the circumference of the lead. As shown in FIGS. 5A-5F, one electrode level, such as one of electrode levels 404 and 414 of leads 400 and 410, are illustrated to show electrode placement around the perimeter, such as around a shaft, or around the longitudinal axis, of the lead relative to primary directions (anterior, posterior, medial, lateral) and secondary directions (anterior-medial, anterior-lateral, posterior-medial and posterior-lateral). In some examples, the primary and secondary directions are determined based on a directional marker, e.g., a radiopaque stripe, tab, detent, or other structure on the lead housing and/or a marking electrode, and the direction of the directional marker and/or marking electrode may be determined based on patient 112 anatomy, e.g., during implantation of the lead or post-operatively. In other examples, the primary and secondary direction may be determined based on a qualified biomarker source location and/or orientation as illustrated in FIG. 5G.

FIG. 5A shows electrode level 500 that includes circumferential electrode 502. Circumferential electrode 502 encircles the entire circumference of electrode level 500 and may be referred to as an annular, ring or omnidirectional electrode in some examples. Circumferential electrode 502 may be utilized as a cathode or anode or for sensing as configured by the user.

FIG. 5B shows electrode level 510 which includes two electrodes 512 and 514. Each electrode 512 and 514 wraps approximately 170 degrees around the circumference of electrode level 510. Spaces of approximately 10 degrees are located between electrodes 512 and 514 to prevent inadvertent coupling of electrical current between the electrodes.

Smaller or larger spaces between electrodes (e.g., less than 10 degrees, or between 10 degrees and 30 degrees) may be provided in other examples. Each electrode 512 and 514 may be programmed to act as an anode or cathode or utilized for sensing. Electrodes may be equal or unequal in geometry. The individual electrodes could be clustered into one or more sets of electrodes to include more than one or all for sensing or stimulation.

FIG. 5C shows electrode level 520 which includes three equally sized electrodes 522, 524 and 526. Each electrode 522, 524 and 526 encompass approximately 110 degrees of the circumference of electrode level 520. Similar to electrode level 510, spaces of approximately 10 degrees separate electrodes 522, 524 and 526. Smaller or larger spaces between electrodes (e.g., less than 10 degrees, or between 10 degrees and 30 degrees) may be provided in other examples. Electrodes 522, 524 and 526 may be independently programmed as an anode or cathode for stimulation or utilized for sensing. Electrodes may be equal or unequal in geometry. The individual electrodes could be clustered into one or more sets of electrodes to include more than one or all for sensing or stimulation.

FIG. 5D shows electrode level 530 which includes four electrodes 532, 534, 536 and 538. Each electrode 532, 534, 536 and 538 covers approximately 80 degrees of the circumference with approximately 10 degrees of insulation space between adjacent electrodes. Smaller or larger spaces between electrodes (e.g., less than 10 degrees, or between 10 degrees and 30 degrees) may be provided in other examples. Electrodes 532, 534, 536 and 538 may be independently programmed as an anode or cathode for stimulation or utilized for sensing. Electrodes may be equal or unequal in geometry. The individual electrodes could be clustered into one or more sets of electrodes to include more than one or all for sensing or stimulation.

Figure 5E:
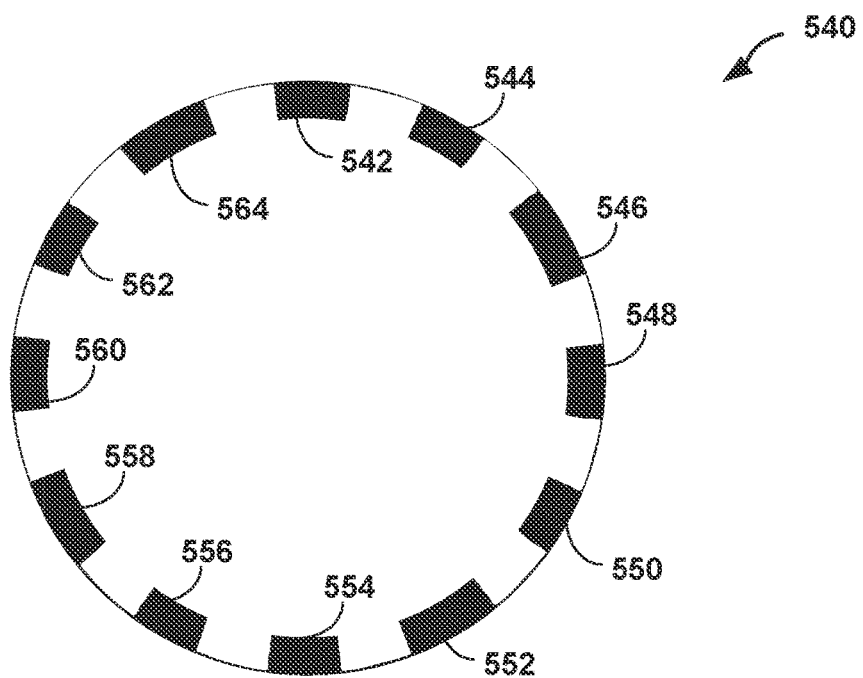

FIG. 5E shows electrode level 540 which includes twelve electrodes 542, 544, 546, 548, 550, 552, 554, 556, 558, 560, 562, and 564. Each electrode 542, 544, 546, 548, 550, 552, 554, 556, 558, 560, 562, and 564 covers approximately 20 degrees of the circumference with approximately 10 degrees of insulation space between adjacent electrodes. Smaller or larger spaces between electrodes (e.g., less than 10 degrees, or between 10 degrees and 30 degrees) may be provided in other examples. Electrodes 542, 544, 546, 548, 550, 552, 554, 556, 558, 560, 562, and 564 may be independently programmed as an anode or cathode for stimulation or utilized for sensing. Electrodes may be equal or unequal in geometry. The individual electrodes could be agglomerated in a set of electrodes to include more than one or all for sensing or stimulation.

Figure 5F:
Figure 5F:
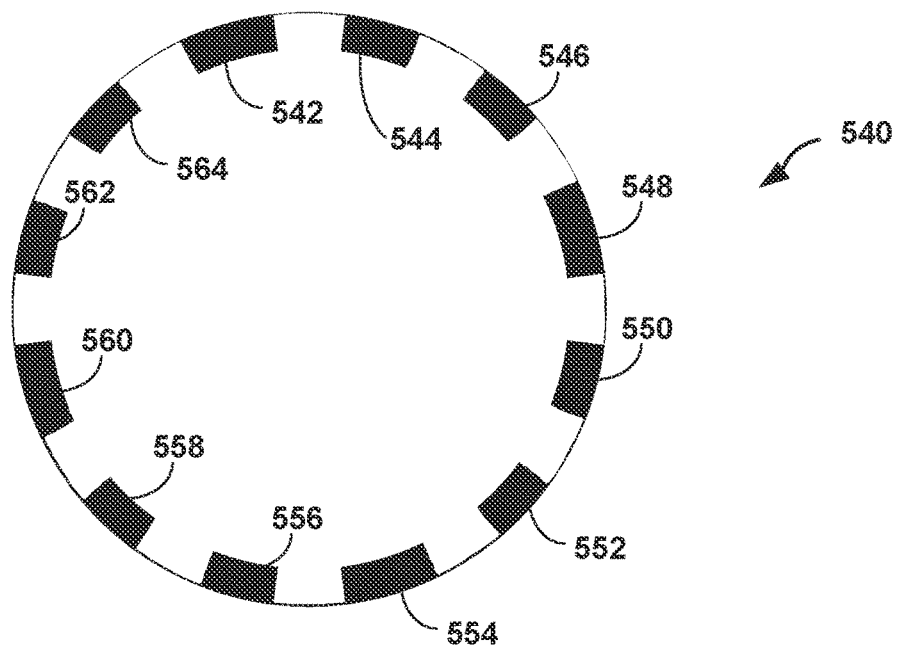
Figure 5G:
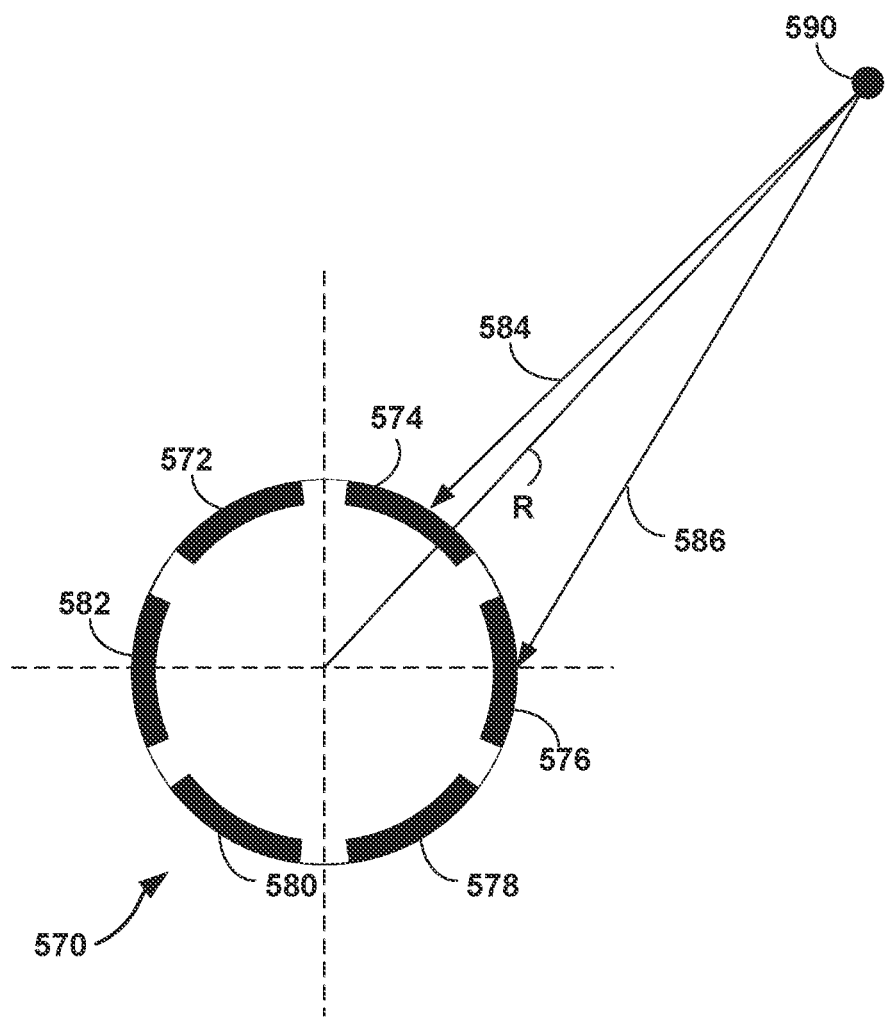

In some examples, the electrodes or electrode cluster or agglomerated sets of electrodes at each level of leads including a plurality of electrodes around the circumference of the lead may be assigned to, classified by, and/or identified by a primary direction and one or more secondary directions, as described below with reference to FIG. 8. In some examples, the primary direction and secondary directions assigned to an electrode may change depending on the orientation of the lead with respect to the directional marker (physical or radiological or sensed signal). FIG. 5F shows electrode level 540 with the lead rotated about 15 degrees relative to the lead illustrated in FIG. 5E along the longitudinal axis of the lead. In some examples, the primary direction and secondary directions assigned to electrodes 542, 544, 546, 548, 550, 552, 554, 556, 558, 560, 562, and 564 of FIGS. 5E and 5F may be different because of the different orientation of the lead with respect to the directional marker, as described below with reference to FIG. 8.

FIG. 5G shows electrode level 570 which includes six electrodes 572, 574, 576, 578, 580, and 582. Each electrode 572, 574, 576, 578, 580, and 582 covers approximately 50 degrees of the circumference with approximately 10 degrees of insulation space between adjacent electrodes. Smaller or larger spaces between electrodes (e.g., less than 10 degrees, or between 10 degrees and 30 degrees) may be provided in other examples. Electrodes 572, 574, 576, 578, 580, and 582 may be independently programmed as an anode or cathode for stimulation or utilized for sensing. Electrodes may be equal or unequal in geometry. The individual electrodes could be agglomerated into a set of electrodes to include more than one or all for sensing or stimulation.

In some examples, the electrodes or set of electrodes at each level of leads including a plurality of electrodes around the circumference of the lead may be assigned to, classified by, and/or identified by a primary direction and one or more secondary directions. In the example shown, the primary direction and secondary directions assigned to electrodes 572, 574, 576, 578, 580, and 582 may be assigned with respect to sensed signal source 590. For example, a reference vector R may be determined from the axis of lead 114 to sensed signal source 590. Electrode radial vectors 584 and 586 may be determined from the center of electrodes 574 and 576, respectively, to the center of sensed signal source 590. Primary and secondary directions for electrodes 574 and 576 may be determined and/or assigned based on an angular difference between electrode radial vectors 584 and 586 with respect to reference vector R. In some examples, primary and secondary directions for each electrode, e.g., 572, 574, 576, 578, 580, and 582 in the example shown, may be determined and/or assigned based on an angular difference between each electrode's radial vector with respect to reference vector R. In some examples, an electrode set could be formed by clustering electrodes, e.g., grouping into one or more electrode sets, which are closely aligned with the radial vector R and the distance of the source to the individual electrode center is lesser than the distance of the source to the lead axis. Conversely in other examples, an electrode set could be formed by grouping electrodes which are closely aligned with the radial vector R and the distance of the source to individual electrode center is greater than the distance of the source to the lead axis.

In other examples, more or fewer electrodes may be included within an electrode level. In alternative examples, consecutive electrode levels of lead 114 may include a variety of electrode levels 500, 510, 520, 530, 540 and 570. For example, lead 114 (or any other lead described herein) may include electrode levels that alternate between electrode levels 510 and 530 depicted in FIGS. 5B and 5D. In this manner, various stimulation field shapes may be produced within brain 120 of patient 112. Further the above-described sizes of electrodes within an electrode level are merely examples, and the present disclosure is not limited to the example electrode sizes.

Also, the insulation space, or non-electrode surface area, may be of any size. Generally, the insulation space is between approximately 1 degree and approximately 20 degrees. More specifically, the insulation space may be between approximately 5 and approximately 15 degrees. In other examples, insulation space may be between approximately 10 degrees and 30 degrees or larger. Smaller insulation spaces may allow a greater volume of tissue to be stimulated. In alternative examples, electrode size may be varied around the circumference of an electrode level. In addition, insulation spaces may vary in size as well. Such asymmetrical electrode levels may be used in leads implanted at tissues that may benefit from certain shaped, fragmented, fractionalized, or directionally steered stimulation fields.

Figure 6:
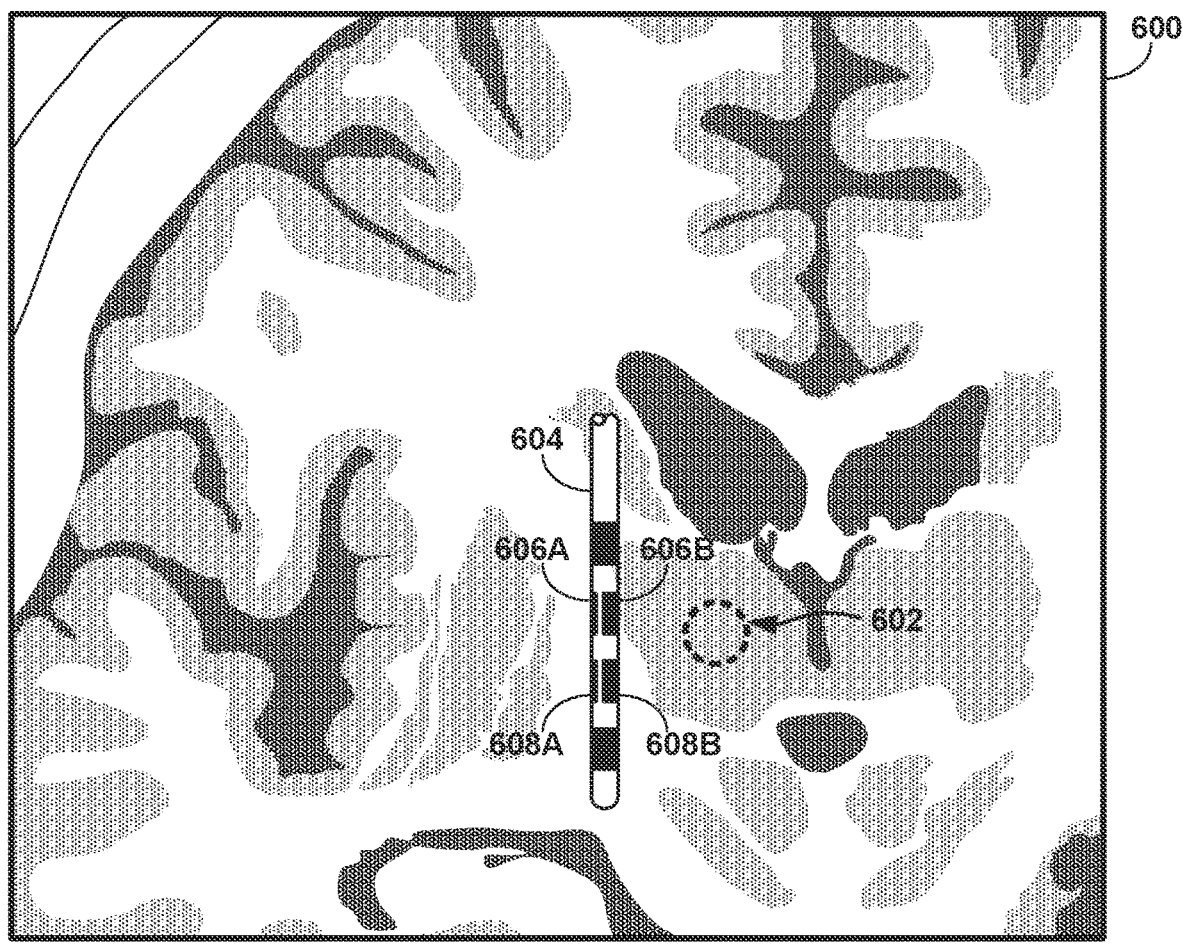
FIG. 6 is a coronal view of example tissue with a lead placed with respect to a target location within tissue.
Figure 6:
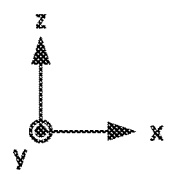

FIG. 6 is a coronal view of example tissue with a lead 604 placed with respect to a target location within tissue. As shown in FIG. 6, a representation of anatomical regions of brain 120 is displayed by coronal view 600. Coronal view 600 is a front-back vertical section of brain 120. Coronal view 600 may be an actual image of brain 120 produced with MRI (e.g. patient specific atlas using a target specific sequence), CT, or another imaging modality (e.g. fused, merged, or co-registered dataset between two modalities or sequences on a neuro-navigation system). Coronal view 600 may be an illustration of the location of a lead with respect to a target tissue from which electrical signals originate (e.g., LFP signal source) (e.g. augmented view on which lead model is overlaid on three dimensional patient specific atlas with structures and connectomes with or without corresponding spatially tagged biomarker locations). In some examples, coronal view 600 may be presented by programmer 104 or another device to indicate the relative position of lead 604 and the electrodes carried by the lead according to the sensed electrical signals. These images thus may be used to identify anatomical regions that may help the clinician program the stimulation parameters.

Coronal view 600 is a 2D coronal slice of brain 120. Differently shaded portions of coronal view 600 indicate varying densities of tissue within brain 120. Darker portions indicate less dense tissue. For example, the darkest portion of coronal view 600 is indicative of spaces within brain 120 that contain cerebrospinal fluid (CSF). White portions of brain 120 indicate dense tissue and more neurons. It should be noted that coronal view 600 is only an example, and actual images may include a wider range of shades at higher image resolution or views in a plurality of different 2D planes. Coronal view 600 provides a perspective view of lead 604 and the anatomical region in which lead 604 is implanted.

As shown in FIG. 6, lead 604 may be a lead icon that represents an actual lead implanted within patient 112. Lead 604 includes electrodes such as electrodes 606A and 606B located at the same longitudinal position and different circumferential positions around the perimeter of lead 604. Electrode 606C cannot be seen because it is located in the backside of lead 604. Similarly, lead 604 includes electrodes such as electrodes 608A and 608B located at the same longitudinal position (but a different level as compared to electrodes 606) and different circumferential positions around the perimeter of lead 604. Electrode 608C cannot be seen because it is located in the backside of lead 604. When electrical signals, such as LFP signals originate from target tissue 602, the largest amplitude and power of the signal will likely be sensed by the electrode or electrodes closest to target tissue 602. In this example, a sensing electrode combination of electrodes 606B and 608B may sense a larger amplitude electrical signal from target tissue 602 than any other electrode combinations on lead 604. In some examples, monopolar sensing may result in electrode 606B sensing the highest amplitude or power of electrical signals from target tissue 602. Other features of the sensed signal like but not limited to, power in specific frequency bands or other time or frequency domain characteristics could be considered relevant depending on the disease characteristics.

Figure 7:
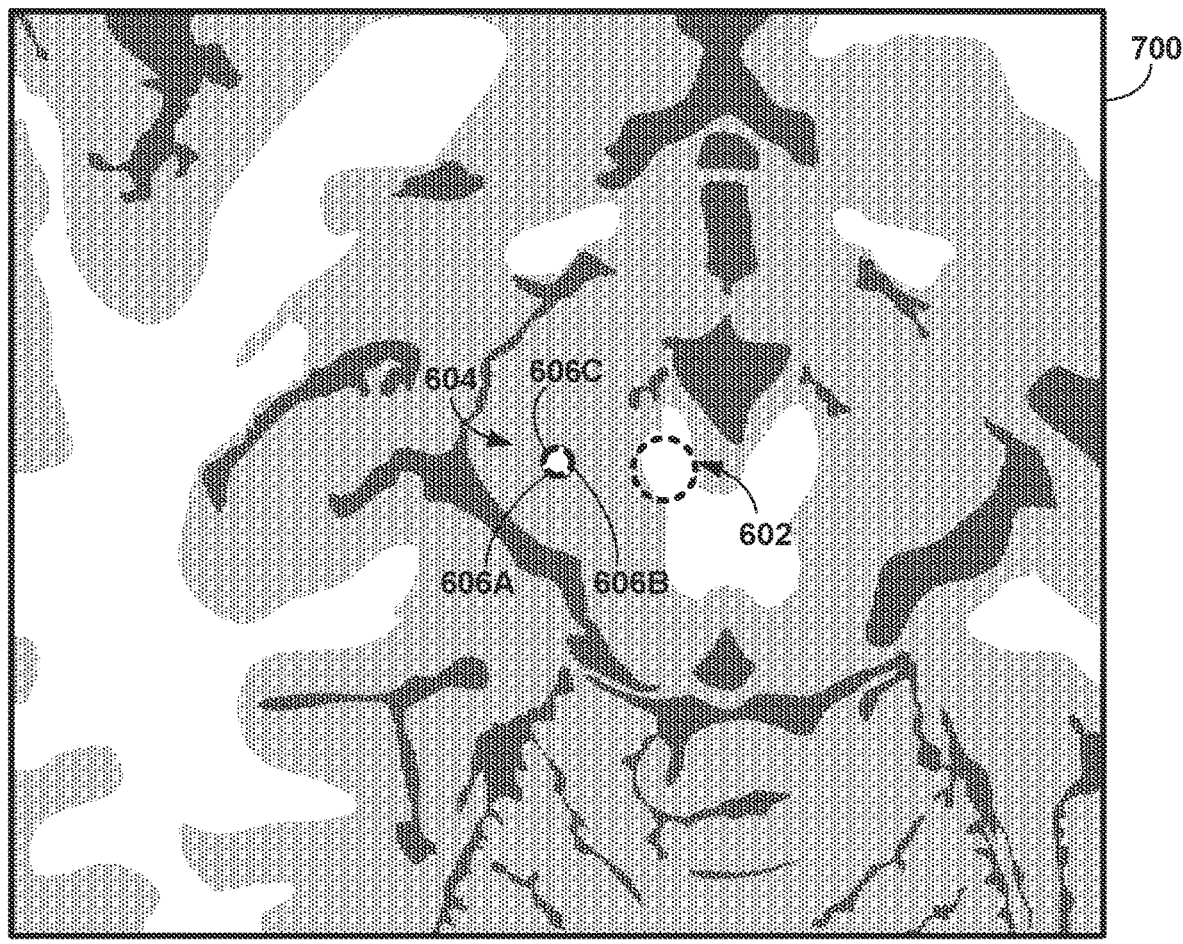
FIG. 7 is an axial view of example tissue with a lead placed with respect to a target location within tissue.

FIG. 7 is an axial view of example tissue with a lead 604 placed with respect to a target tissue 602. Axial view 700 is a different view of tissue than coronal view 600. Axial view 700 also shows the cross-sectional view of lead 604 and electrodes 606A, 606B, and 606C. As shown in axial view 700, electrode 606B is closest to target tissue 602 and may register the largest amplitude/power of sensed electrical signals when compared to the remaining electrodes of lead 604. If lead 604 were to rotate within tissue due to patient movement, lead pull, or some other force, a different electrode, such as electrode 606A, may be located closest to target tissue 602 and sense electrical signals with the largest amplitude/power when compared to other electrodes. Alternately in some degenerative neurological conditions the target tissue 602 may itself undergo changes during the disease life cycle. Even though the lead is fixed firmly with respect to the cranium 122, sensed signal source direction may have changed due to a change in the morphology of target tissue 602. Although FIGS. 6 and 7 discuss electrical signals that may originate in tissue, the same spatial origin may be used when sensing electrical signals evoked from delivered stimulation or sensing delivered stimulation itself for determining lead movement.

Figure 8:
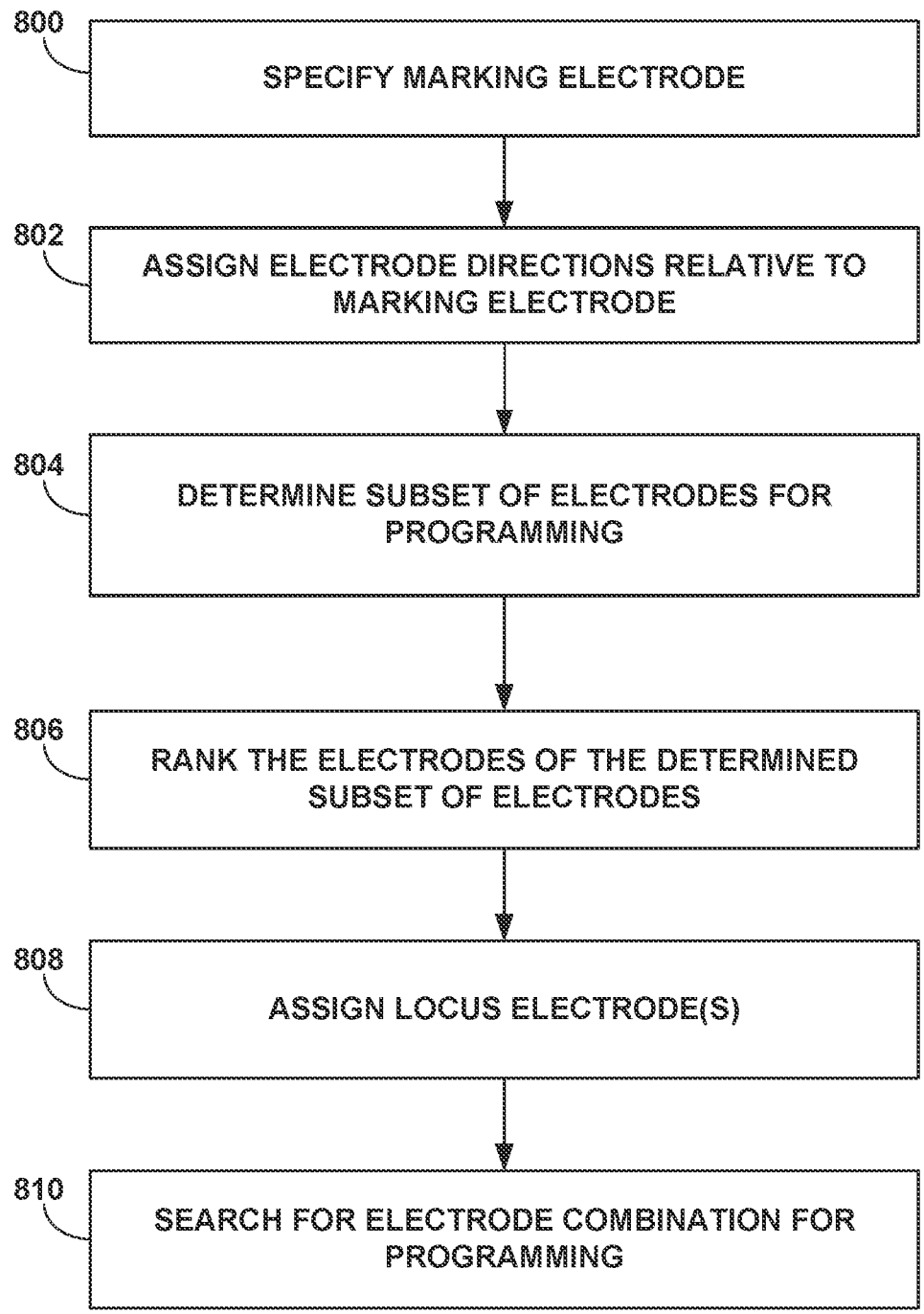
FIG. 8 is a flowchart illustrating an example method for programming a medical device according to an example of the techniques of the disclosure.

FIG. 8 is a flowchart illustrating an example method for programming a medical device according to an example of the techniques of the disclosure. The example of FIG. 8 is described with respect to processing circuitry 310 of programmer 104. However, other devices, systems, or combinations thereof, may perform the technique of FIG. 8 in other examples. In addition, a clinician or other user may perform one or more steps alone or in conjunction with a device. In the example shown, a clinician and/or user may specify a marking electrode (800). In some examples, the clinician and/or user may specify directional marker for ascertaining spatial orientation relative to anatomy within which the electrode is implanted at the time of lead implantation or post-operatively. For example, the medical device may include one or more leads, e.g., leads 114A and 114B. Each of the leads may include one or more electrodes at each of one or more levels mounted at various lengths of lead housing, for example, as illustrated and described above with respect to FIG. 4. The lead housing on each of the one or more leads may include one or more directional markers, for example, one or more of the electrodes, a radiopaque stripe, a tab, detent, or other structure on the outside of the lead housing, such as described above with reference to FIG. 4. A clinician and/or user may use an intra-operative imaging technique, e.g., lateral fluoroscopy, O-Arm™, CT, and the like, to identify the directional marking during and/or after implantation of the lead. In some examples, a clinician and/or user may predetermine a spatial orientation of the lead before implantation. For example, a clinician and/or user may create a patient specific atlas from atlas from target-specific high-resolution MRI image sequences, or a clinician and/or user may determine the most optimal steering direction for lead implantation using acute intra-operative recording to identify the source of a qualified biomarker and directional acute intra-operative test stimulation. In some examples, a clinician and/or user may mechanically steer the lead by manually orienting the lead intracranially during implantation and verify lead orientation via the directional marker, e.g., via a radiopaque stripe and imaging. In some examples, a clinician and/or user may implant a segmented lead through a cannula reaching up to the target, or a predetermined distance above the target, to enable mechanical lead steering and to ensure that a predetermined lead orientation, e.g., the predetermined lead orientation being determined via imaging, electrophysiology, or both.

Once the lead is implanted and the orientation of the lead is determined as described above, the clinician, user, and/or processing circuitry such as processing circuitry 310, may assign/specify/designate one or more marker electrodes (800). In some examples, the marker electrode may be the directional marker. In other examples, the marker electrode may be specified, and its direction determined based on the orientation of the lead determined via the directional marker, the directional marker orientation being specified relative to anatomy within which the marker electrode is implanted, e.g., as described above. In some examples, the orientation of each of the electrodes of the lead may be predetermined and known relative to each other, such that once the directional marker is specified and its orientation/direction determined based on the directional marker, the orientation/direction of each of the electrodes of the lead may be determined based on the marker electrode. In other examples the marker electrode or the directional marker may be identified as the one most pertinent (e.g. closest, farthest or intermediate) to the source/sources of a sensed biomarker signal characteristic (e.g. frequency band power spectrum, phase shift, frequency shift within a band etc.).

In some examples, processing circuitry 310 may determine the orientation of the lead relative to a reference direction. In some examples, the reference direction may be relative to anatomy of patient 112. For example, the reference direction may be any of anterior, posterior, medial, and lateral based on the patient 112 planes of reference, e.g., the coronal, sagittal, and transverse planes of patient 112, and the orientation of the lead may be determined based on an angle between the direction of the directional marker and any of the primary directions of patient 112. In some examples, the reference direction may be specified based on a sensed signal source within patent 112, such as LFPs from a source within patient 112 anatomy such as brain 120. In some examples, the direction of the directional marker may be specified as the reference direction, and in other examples the marking electrode may be specified as the reference direction.

In some examples, processing circuitry 310 may assign a primary direction and one or more secondary directions to each of the electrodes of each of the leads based on the marking electrode and reference direction (802). For example, processing circuitry 310 may assign each electrode to one primary direction, e.g., anterior, posterior, medial, and lateral as illustrated and described above with reference to FIGS. 5E-5F. Processing circuitry 310 may assign each electrode to one or more secondary directions, e.g., anterior-medial, anterior-lateral, posterior-medial and posterior-lateral.

In some examples, processing circuitry 310 may group the electrodes into sets of electrodes based on assigned primary and secondary directions. In some examples, processing circuitry 310 may assign each electrode to a primary and/or secondary direction based on how close the direction of the electrode is to the primary and/or secondary direction, e.g., the primary and/or secondary direction with a minimum difference to the direction of the electrode. In some examples, processing circuitry 310 may group each electrode into one primary direction set of electrodes and one or more secondary direction set of electrodes. By way of example with reference to FIG. 5E, processing circuitry 310 may assign each of electrodes 564, 542, and 544 of lead 540 to an anterior primary direction, e.g., based on their determined orientation relative to the primary directions via 800 and 802. Processing circuitry 310 may group electrodes 564, 542, and 544 into an anterior direction set of electrodes based on their assigned primary direction. Similarly, processing circuitry 310 may assign each of electrodes 546, 548, and 550 to a medial primary direction and group electrodes 546, 548, and 550 into a medial direction set of electrodes, assign each of electrodes 552, 554, and 556 to a posterior primary direction and group electrodes 552, 554, and 556 into a posterior direction set of electrodes, and assign each of electrodes 558, 560, and 562 to a lateral primary direction and group electrodes 558, 560, and 562 into a lateral direction set of electrodes. In the example shown, processing circuitry 310 may assign and group electrodes 544 and 546 into an anterior-medial secondary direction and set of electrodes, electrodes 550 and 552 into a posterior-medial secondary direction and set of electrodes, electrodes 556 and 558 into a posterior-lateral secondary direction and set of electrodes, and electrodes 562 and 564 into an anterior-lateral secondary direction and set of electrodes. However, in the example shown, electrodes 542, 548, 554, and 560 may be equidistant in direction from two secondary directions and processing circuitry 310 may assign 542, 548, 554, and 560 to one or both secondary directions and sets of electrodes. For example, processing circuitry 310 may assign and group electrode 542 into both the anterior-lateral and anterior-medial directions and sets of electrodes, electrode 548 into both the anterior-medial and posterior-medial directions and sets of electrodes, electrode 554 into both the posterior-lateral and posterior-medial directions and sets of electrodes, and electrode 560 into both the posterior-lateral and anterior-lateral directions and sets of electrodes.

In some examples, if the lead is rotated and/or oriented differently with respect to surrounding anatomy, the combination of electrodes to efficiently and effectively provide stimulation to target regions may be different. Accordingly, processing circuitry 310 may assign the electrodes to different primary and secondary directions and group the electrodes into different primary and secondary sets of electrodes because the electrodes are positioned and/or directionally oriented differently with respect to surrounding anatomy. FIG. 5F illustrates an example of lead 540 rotated relative to the example illustrated in FIG. 5E, e.g., counterclockwise about 15 degrees. Processing circuitry 310 may assign each of electrodes 542 and 544 of lead 540 to an anterior primary direction, e.g., based on their determined orientation relative to the primary directions via 800 and 802. Processing circuitry 310 may group electrodes 542 and 544 into an anterior direction set of electrodes based on their assigned primary direction. Similarly, processing circuitry 310 may assign and group electrodes 548 and 550 into a medial primary direction and a medial direction set of electrodes, electrodes 554 and 556 into a posterior primary direction and a posterior direction set of electrodes, and electrodes 560 and 562 into a lateral primary direction and grouped into a lateral direction set of electrodes. In the example shown, electrodes 546, 552, 558, and 564 may be equidistant in direction from two primary directions. In contrast to electrodes 542, 548, 554, and 560 of FIG. 5E in which processing circuitry 310 assigned multiple, e.g., two, secondary directions to those electrodes, processing circuitry 310 may assign a single primary direction to electrodes 546, 552, 558, and 564 of FIG. 5F. In some examples, processing circuitry 310 may assign each of electrodes 546, 552, 558, and 564 to a primary direction different from each other, e.g., one of electrodes 546, 552, 558, and 564 may be assigned per primary direction such that each of the four primary direction sets of electrodes would include three of the twelve electrodes in the example shown. In other examples, processing circuitry 310 may assign more than one of electrodes 546, 552, 558, and 564 to the same primary direction, e.g., as illustrated in Table 1 below. For example, processing circuitry 310 may assign electrodes 564 and 546 to the anterior direction and electrodes 552 and 558 to the posterior direction, and the anterior and posterior primary direction sets of electrodes may each include four of the twelve electrodes and the medial and lateral directions may each include two of the twelve electrodes. Processing circuitry 310 may assign each of the electrodes to one or more secondary directions and sets of electrodes in a similar manner, although not to the same directions and sets of electrodes, as described above with reference to FIG. 5E. By way of comparison, the example sets of electrodes for lead 540 for each of the examples illustrated in FIG. 5E and FIG. 5F are shown below in Table (1).

specific areas/regions, e.g., to identify electrodes or directional sets of electrodes that may be more optimal to be considered for programming. In some examples, each individual electrode and/or the primary and secondary directional sets of electrodes may be coarsely ranked. Alternately a clinician, user, and/or processing circuitry 310 may determine a coarse ranking of the electrodes based on the sensed biomarker signal characteristics, e.g., power in a specific frequency band, phase shift, frequency shift within a band, source location and alignment, other time/frequency domain characteristics, result of mathematical operation between the recordings from two or more sources like the summation or difference or correlation or entrainment, evoked resonant response etc. In certain disease states, the sensed biomarker (1)

|  | Primary | | | | Secondary | | | |
| --- | --- | --- | --- | --- | --- | --- | --- | --- |
|  | Anterior | Medial | Posterior | Lateral | Anterior-Medial | Posterior-Medial | Posterior-Lateral | Anterior-Lateral |
| FIG. 5E | 564, 542, 544 | 546, 548, 550 | 552, 554, 556 | 558, 560, 562 | 542, 544, 546, 548 | 548, 550, 552, 554 | 554, 556, 558, 560 | 560, 562, 564, 542 |
| FIG. 5F | 564, 542, 544, 546 | 548, 550 | 552, 554, 556, 558 | 560, 562 | 544, 546, 548 | 550, 552, 554 | 556, 558, 560 | 562, 564, 542 |

Table 1 is one example of grouping electrodes into directional sets of electrodes, in other examples, the groupings may be different. For example, the primary sets of electrodes for FIG. 5F may have three electrodes each if one of electrodes 546, 552, 558, and 564 are assigned to a primary direction different from each other. Grouping, clustering or agglomerating individual electrodes into directional sets of electrodes could follow varied approaches to collimate the stimulation in order to steer the fractionalized energy and focus/converge it more narrowly or diffuse the same in overlapping directions based on patient specific anatomy or a sensed signal characteristic.

With reference to FIG. 8, a clinician, user, and/or processing circuitry 310 may determine a subset of electrodes for programming (804). For example, a clinician, user, and/or processing circuitry 310 may determine a coarse ranking of the electrodes based on the location and the direction of each of the electrodes relative to one or more target regions. In some examples, the clinician, user, and/or processing circuitry 310 may determine the location and the direction, e.g., relative to the leads and/or electrodes, via a post-operative conditionally safe MRI scan, a pre-operative Mill and a post-operative CT scan fusion on a neuro-navigation system or on a visual programming platform, e.g., SureTune™. Target regions may include tissue and/or structures to be stimulated via one or more electrodes, or tissue and/or structures to be exempted from stimulation for which stimulation via one or more electrodes may cause side-effects. For example, specific areas/regions in the sub-territory of each target may be "sweet/hot spots" identified retrospectively in a cohort of patients using aggregation, such as probabilistic statistical maps. Stimulation of the specific areas/regions may improve a patient dominant sub-symptom of Parkinson's disease, e.g., rigidity, bradykinesia, tremor, and the like. In some example, a clinician, user, and/or processing circuitry 310 may coarsely rank the electrodes based on location and direction with respect to the signal characteristics may be an indicator of the brain, disease or symptom state in response to medication or stimulation.

After coarse ranking, processing circuitry 310 may select a subset of electrodes for programming based on the coarse ranking, and the unselected and/or excluded electrodes may be unused for stimulation programming. For example, processing circuitry 310 may select the subset of electrodes based on a ranking threshold and/or a predetermined number of electrodes allowed for the subset, or any other criteria. In some examples, selecting a subset of electrodes for programming, and excluding one or more electrodes for programming based on the coarse ranking and/or directional sets of electrodes of electrodes may reduce the complexity of programming or re-programming.

After determining a subset of electrodes for programming based on the coarse ranking, processing circuitry 310 may determine a stimulation ranking of the electrodes of the subset of electrodes (806). In some examples, the processing circuitry 310 may determine the stimulation ranking of the electrodes of the subset of electrodes using multiple criteria optimization, e.g., via determining a score based on an inferred electrical efficiency and therapeutic window for each monopolar configuration of electrodes. In some examples, processing circuitry 310 may determine multiple criteria optimization based on physiological effects, e.g., an alleviation of symptoms as assessed by a clinician and/or neurologist and, in some example, with insight from a sensed biomarker signal such as LFPs or a resonant response. In some examples, multiple criterial optimization may include assessing the inclusion or exclusion of certain anatomical areas in the patient specific atlas integrated with the volume of neuronal activation (VNA) and/or volume of tissue activated (VTA) or volume of electrostatic field, e.g., visually using a visual programming platform such as Sure-Tune™. In some examples, the stimulation ranking may be based on the electrodes scores and the electrode scores may be based on one or both of an electrical efficiency (effect threshold) and therapeutic window.

For example, processing circuitry 310 may determine an electrical efficiency according to the minimum electrical stimulation amplitude of a monopolar configuration of electrodes that results in beneficial effects, e.g., alleviation of symptoms, also sometimes referred to sometimes as the effect threshold. The clinician, user, and/or processing circuitry 310 may determine a therapeutic window based on a difference between the electrical stimulation amplitude of a monopolar configuration of electrodes that results in side-effects and the minimum electrical stimulation amplitude of a monopolar configuration of electrodes that elicits beneficial effects, e.g., the electrical efficiency. In other words, the therapeutic window is the electrical stimulation amplitude difference between the amplitude at which benefits begin (usually a lower amplitude) and the amplitude at which unwanted side-effects are induced (usually higher). In some examples, processing circuitry 310 may determine an electrical efficiency and therapeutic window as IMD 106 "ramps up" electrical stimulation amplitude. If the benefits occur at a lower amplitude than the side-effects, the therapeutic window is positive. In some examples, the system, patient, or clinician may adjust the amplitude within the therapeutic window to fine tune therapy. If the side-effects occur at a lower amplitude than the benefits, the therapeutic window is zero (e.g., the sweep of amplitude up will be stopped and not get to beneficial values) and stimulation using that configuration may be determined to be not beneficial. In some examples, the electrical efficiency and therapeutic window may be defined by other parameters of electrical stimulation. For example, the electrical efficiency may be the minimum electrical stimulation pulse width, pulse rate, and/or frequency of a monopolar configuration of electrodes that results in beneficial effects, and the therapeutic window may be the difference between the pulse width, pulse rate, and/or frequency at which the monopolar configuration of electrodes results in side-effects and the minimum electrical stimulation pulse width, pulse rate, and/or frequency of a monopolar configuration of electrodes that results in beneficial effects, e.g., the electrical efficiency. In other words, the electrical efficiency and therapeutic window may be based on electrical stimulation charge, power or intensity, e.g., the amount of electrical energy applied to tissue, e.g., any of a higher amplitude, pulse rate, frequency, and pulse width of electrical stimulation resulting in a higher electrical energy applied (values could be adjusted to include impedance of each of the individual electrodes or sets of electrodes). In some examples, the electrical efficiency may be the minimum electrical stimulation dose of a monopolar configuration of electrodes that results in beneficial effects, and the therapeutic window may be the difference between the electrical stimulation dose at which the monopolar configuration of electrodes results in side-effects and the minimum electrical stimulation dose of a monopolar configuration of electrodes that results in beneficial effects, e.g., the electrical efficiency. Evoked signals like the resonant response or sensed signals like intrinsic sensed biomarkers with or without stimulation (e.g., acute or chronic signals depending on the latency of response) could be recorded to identify the onset of benefits and induction of side-effects. If other alternate electrode configurations are deemed relevant by the clinician in a specific disease condition then other configurations not only limited to like wide/narrow bipolar, double monopolar, guarded cathode, tri or tetra polar, anodic stimulation etc. could also be evaluated. Configurations could also be based on the shape of the volume of neural activation (VNA), volume of tissue activation (VTA), or volume of electrostatic field necessary in the target tissue for a specific disease condition or the need to specifically target a sub-territory of the target tissue for alleviation of a particular symptom or the need to specifically avoid an anatomical structure/sub-territory of the target tissue.

The clinician, user, and/or processing circuitry 310 may determine a score based on the electrical efficiency and therapeutic window, e.g., a score may be calculated as 1−(electrical efficiency/therapeutic window), where (electrical efficiency/therapeutic window) is the ratio of the electrical efficiency value to the therapeutic window value. The clinician, user, and/or processing circuitry 310 may determine a score for individual electrodes of the subset of electrodes and/or a grouping of electrodes in a monopolar configuration, e.g., a directional cluster or a set of electrodes.

Table (2) illustrates an example stimulation ranking of a lead including segmented ring electrodes while maintaining the same frequency and pulse width across all Options, e.g., configurations. In Table (2) below, Option 1, 2, 3, and 4 may be an individual electrode or a monopolar configuration of a plurality of electrodes or any other configuration for sets of electrodes. In Table (2) below, Options 1, 2, 3, and 4 may identify single electrodes or may identify, or be used for, electrode combinations e.g. sets of electrodes or clusters. As shown, the Score may be a positive or a negative value, and the Stimulation Rank is based on the highest Score.

| | (2) | | | |
|---|---|---|---|---|
| Option | Electrical Efficiency (Volts) | Therapeutic Window (Volts) | Score | Stimulation Rank |
| 1 | 1.5 | 3 | 0.5 | 2 |
| 2 | 1 | 3 | 0.667 | 1 |
| 3 | 2.5 | 1 | −1.5 | 3 |
| 4 | 3 | 1 | −2 | 4 |

After determining a stimulation ranking of the electrodes of the subset of electrodes, the clinician, user, and/or processing circuitry 310 may assign a locus electrode for one or more of the primary and secondary directions (808). For example, the clinician, user, and/or processing circuitry 310 may assign a locus electrode of a direction based on the stimulation ranking of the electrodes having the same primary and/or secondary direction assigned. In some examples, the clinician, user, and/or processing circuitry 310 may assign the electrode closest to a target region (or sensed source) in position and direction as the locus electrode for that direction.

After assigning a locus electrode for one or more of the primary and secondary directions, the clinician, user, and/or processing circuitry 310 may determine a stimulation electrode combination, e.g., for programming (810). In some examples, the clinician, user, and/or processing circuitry 310 may determine a stimulation electrode combination based on a dynamically minimalistic search. For example, the clinician, user, and/or processing circuitry 310 may cause stimulation via the fewest number of electrodes of a directional set of electrodes, e.g., the single locus electrode, and gradually adding more electrodes to improve clinical efficacy. For example, electrodes of the same primary directional set of electrodes may be added, e.g., based on a minimum positional difference relative to the locus electrode, and electrodes of the same secondary directional set of electrodes may be added next, e.g., based on a minimum positional difference relative to the locus electrode. Additionally, electrodes congruent with the locus and locus array may be added. In some examples, a locus array comprises electrodes that share a common factor, e.g., a primary and/or secondary assigned direction, a disease specific biomarker sensed signal, direction specific to a target anatomy or sub-region within a target tissue and/or structure, and the like. In some examples, electrodes congruent to the locus electrode and/or locus array may assist in altering the characteristics of the sensed biomarker signal when those electrodes are activated alongside the locus electrode. For example, if there is more than one source of a qualified biomarker detected and/or sensed, the locus electrode may be the electrode pointing in the direction of the dominant biomarker and congruent electrodes may be the electrodes pointing in the direction of the source but having a lesser span and smaller angular variation to its center with reference to the dominant biomarker. If more than one coherent source is identified, congruent electrodes may point in the direction of a lesser dominant source. The clinician, user, and/or processing circuitry 310 may stop adding electrodes when no further reduction in symptoms is obtained or if an undesirable side-effect is induced or if there are no relevant changes being recorded in the sensed signals.

In some examples, clinician, user, and/or processing circuitry 310 may determine a stimulation electrode combination based on a systematically reductive search. For example, the clinician, user, and/or processing circuitry 310 may cause stimulation via a starting plurality of electrodes forming the stimulation electrode combination, e.g., for programming. In some examples, the starting plurality of electrodes may include all of the electrodes with the same primary and/or secondary directions or all electrodes pointing in the direction of a sensed signal source or sometimes include all electrodes to deliver omnidirectional stimulation. The clinician, user, and/or processing circuitry 310 may gradually remove electrodes from providing stimulation, e.g., minimizing the number of electrodes providing stimulation to improve electrical efficiency, reduce undesirable induced side-effects while still providing clinical efficacy, a reduction in symptoms and/or if there are no relevant changes being recorded in the sensed signals. In some examples, clinician, user, and/or processing circuitry 310 may use guidance from VNA, VTA, volume of electrostatic field and side-effects in determining whether to continue removing electrodes from the plurality of electrodes forming the stimulation electrode combination. The clinician, user, and/or processing circuitry 310 may stop removing electrodes when no further reduction in side-effects is obtained while still providing a reduction of symptoms or if there are no relevant changes being recorded in the sensed signals.

In some examples, a dynamically minimalistic search and/or a systematically reductive search may be used with high-resolution segmented leads and/or low-resolution segmented leads. In some examples, the VTA of the tissue activated with the final stimulation electrode combination may be plotted via visual programming software, e.g., SureTune™, to confirm that the combination is optimally delivering stimulation to the target regions(s) while avoiding stimulation of undesirable anatomical structures/sub-regions. In some examples, the final stimulation electrode combination determined via the step above may improve directional fractionalization of current, e.g., in combination with a sensed signal biomarker such as LFPs in a certain disease state.

Figure 9:
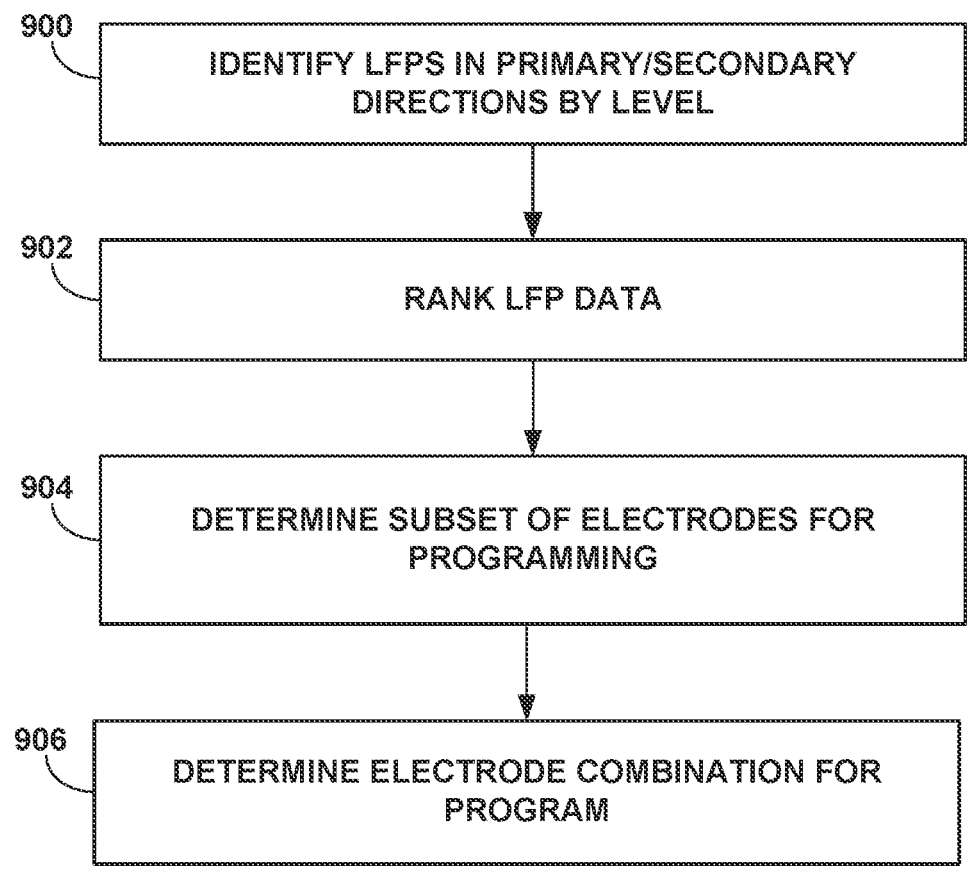
FIG. 9 is a flowchart illustrating an example method for programming a medical device according to an example of the techniques of the disclosure.

FIG. 9 is a flowchart illustrating an example method for programming a medical device according to an example of the techniques of the disclosure. The example of FIG. 9 is described with respect to processing circuitry 310 of programmer 104. However, other devices, systems, or combinations thereof, may perform the technique of FIG. 9 in other examples. In addition, a clinician or other user may perform one or more steps alone or in conjunction with a device. The example method shown may be an illustrative approach for programming IMD 106 using the techniques and/or method illustrated in FIG. 8

In the example shown, a clinician, user, and/or processing circuitry 310 may identify a sensed signal biomarker such as LFPs in the primary and secondary directions, e.g., anterior, posterior, medial, and lateral, anterior-medial, anterior-lateral, posterior-medial and posterior-lateral directions, and by electrode level, e.g., electrode levels such as illustrated in FIG. 4 (900). In some examples, a clinician, user, and/or processing circuitry 310 may logically divide and/or split the lead vertically, e.g., along the superior-inferior axis, into equidistant levels to logically organize the electrodes according to a vertical scrolling scheme. Processing circuitry 310 may logically split the lead based on predetermined value to ensure specificity and sensitivity to LFPs, or a similar biomarker, for a given clinical indication, symptom and target. In some examples, processing circuitry 310 may cause IMD 106 to perform a "horizontal sweep" for LFPs in the beta and gamma bands, e.g., for each electrode around the circumference of the lead, at each level. In some examples, processing circuitry 310 may additionally cause IMD 106 to examine across frequencies the power spectra for LFPs. In some examples, processing circuitry may record, or may cause IMD 106 to record LFPs (e.g., intrinsic signals or evoked signals) while cross referencing each electrode or electrode set to other electrodes or electrode sets, while cross referencing to a contralateral reference electrode, or while cross referencing to an ipsilateral electrode well above, e.g., outside the target area, with or without differential recording. In some examples, the vertical scrolling and horizontal sweeping may assist and/or improve determination of the spatial location of a qualified biomarker source.

In some examples, processing circuitry 310 may derive a vector between an electrode/electrode center, the lead/lead axis, and/or an electrode configuration and a source/target location, e.g., vector reference R as illustrated in FIG. 5G. For example, while differential LFPs are being recorded from segmented leads, polarities may be reversed, e.g., either of the individual electrode segments in a low-resolution segmented lead or a set of electrodes center of a high-resolution segmented lead. Processing circuitry 310 may determine a Fourier Transform and convert the LFP data from the time domain to the frequency domain. Processing circuitry 310 may determine any or all of a phase frequency power spectrum, a phase shift, a time power spectrum, a time frequency power spectrum, a power spectral density, and the like, of the LFPs. For example, the phase difference along with the power variation for the same frequency bands may provide information as to the proximity of the source/target to a specific electrode and/or electrode segment and/or center of electrode set. In some examples, for a reversed set of recordings from the same electrode pairs, e.g., individual electrode segments or centers of electrode sets, a phase delay with lower power in the same frequency band may imply that a source/target is farther away, e.g., the magnitude of the vector may be greater. Conversely, in some examples, a phase lead in comparison with the reversed set along with a higher power in the same frequency band may imply that a source/target is closer, e.g., the magnitude of the vector may be less. In some examples, the determination of a vector between an electrode, the lead, and/or an electrode configuration and a source/target location may assist and/or improve determination of the directional orientation of the electrode/lead/electrode configuration with respect to a tissue source/target.

In some examples, there may be a carry forward effect of stimulation which may be acute or chronic. As such, in some examples, processing circuitry 310 may begin, or cause IMD 106 to begin, stimulation testing at a vertical scroll level and a horizontal sweep direction corresponding to the lowest and/or weakest LFP power in the beta frequency band. Processing circuitry 310 may then proceed to, or cause IMD 106 to gradually and systematically screen each of the vertical levels and horizontal directions in an ascending and/or strengthening LFP power in the beta band. In some examples, different frequency bands may be used for identifying sensed signals or a maximally informative frequency band could be determined. Additionally, processing circuitry 310 may, or cause IMD 106 to determine the gamma band harmonic to assess the emergence of stimulation induced side-effects and/or native frequency at each of the vertical levels and horizontal directions as a best approximation to stimulate during testing.

In some examples, processing circuitry 310 may then rank the electrodes and/or electrode configurations based on the recorded LFP data and/or determined vector and/or vectors (902). For example, processing circuitry 310 may rank the electrodes and/or electrode configurations in an ascending or a descending order of the relevant frequency band or bands and corresponding power and may tag each electrode and/or electrode configuration with directional and/or spatial information, e.g., a primary direction, a secondary direction, and/or a vector. In some examples, this ranking may be analogous to the coarse ranking described above with reference to FIG. 8 at 804. The LFP data sensed may also be used to identify one or more pulse frequencies, pulse widths, amplitudes, etc. for which processing circuitry 310 should determine therapeutic windows and/or electrical efficiency in the following steps. Time-power spectrogram, power spectral density plot or time-frequency-power spectrogram along with LFP scenery and/or frequency specific topographical distribution may also be used in ranking.

In some examples, processing circuitry 310 may then determine a subset of the electrodes for programming (904). For example, processing circuitry 310 may determine the subset based on the ranking described in 902 above. In some examples, processing circuitry 310 may then determine an electrode combination for programming (906). For example, processing circuitry may then perform method steps 806-810 described above using the determined subset of electrodes of method step 904. In some examples, processing circuitry 310 may perform a check that the locus or set of electrodes described according to steps 806-810 of FIG. 8 corresponds to the vector identified from the LFPs in step 900. This check may confirm that higher scoring electrodes (e.g., higher efficiency and wider therapeutic window) are also appropriately positioned to treat the target tissue corresponding to the determined vector based on the sensed LFP data.

The following examples are described herein.

Example 1. A system comprising processing circuitry configured to: determine, for each respective set of electrodes of a plurality of sets of electrodes, a score based on a ratio of an electrical efficiency for the respective set of electrodes to a therapeutic window for the respective set of electrodes; determine, based on the score of each respective set of electrodes, a ranking of the plurality of sets of electrodes; and select, based on the ranking, a subset of the plurality of sets of electrodes for delivery of electrical stimulation therapy.

Example 2. The system of example 1, wherein the plurality of sets of electrodes is a second plurality of sets of electrodes, and wherein the processing circuitry is further configured to, prior to determining the score: assign, based on a reference direction relative to a patient's anatomy and/or a sensed signal source, a primary direction to each respective set of electrodes of a first plurality of sets of electrodes; determine, based on a target location, a location of each respective set of electrodes of the first plurality of sets of electrodes; and exclude, based on the determined location and the assigned primary direction, at least one set of electrodes of the first plurality of sets of electrodes from the second plurality of sets of electrodes, wherein the second plurality of sets of electrodes does not include the excluded at least one set of electrodes.

Example 3. The system of example 2, wherein the processing circuitry is further configured to: determine a directional orientation of a reference set of electrodes relative to a patient's anatomy during an implantation procedure or programming session, wherein the reference direction is based on the directional orientation of the reference set of electrodes to anatomy or the sensed signal source.

Example 4. The system of example 2, wherein the processing circuitry is further configured to, prior to determining the score: assign, based on the reference direction, a secondary direction to each respective set of electrodes of the first plurality of electrodes; and exclude the at least one set of electrodes from the first plurality of sets of electrodes by excluding, based on the determined location and the assigned secondary direction, the at least one set of electrodes of the first plurality of sets of electrodes from the second plurality of sets of electrodes.

Example 5. The system of example 4, wherein the processing circuitry is further configured to: assign, based on the ranking, a locus set of electrodes for at least one of the primary direction or the secondary direction; and select, based on the locus set of electrodes, the subset of electrodes from the second plurality of sets of electrodes.

Example 6. The system of example 5, wherein the processing circuitry is further configured to: control a medical device to deliver the electrical stimulation therapy via a stimulation set of electrodes including only the locus electrode; determine a reduction in symptoms or an increase of a side-effect in response to the delivered electrical stimulation; and repeatedly add, based on the lack of reduction in symptoms or the non-induction of increase of in the side-effect, at least one other set of electrodes from the subset of electrodes to the stimulation set of electrodes, deliver electrical stimulation via the stimulation set of electrodes, and determine a reduction in symptoms or an increase of a side-effect is induced in response to the delivered electrical stimulation.

Example 7. The system of example 5, wherein the processing circuitry is further configured to: control a medical device to deliver the electrical stimulation therapy via a stimulation set of electrodes including the subset of electrodes; determine based on a reduction in symptoms or a decrease of a side-effect in response to the delivered electrical stimulation; and repeatedly remove, based on the reduction in symptoms or the decrease of the side-effect, at least one other set of electrodes from the stimulation set of electrodes, deliver electrical stimulation via the stimulation set of electrodes, and determine a reduction in symptoms or an decrease of a side-effect in response to the delivered electrical stimulation.

Example 8. The system of example 1, wherein the processing circuitry is further configured to: determine the electrical efficiency for each respective set of electrodes based on a minimum electrical amplitude of the respective set of electrodes that results in a beneficial effect for a patient.

Example 9. The system of example 1, wherein the processing circuitry is further configured to: determine the therapeutic window for each respective set of electrodes is based on a difference between a first electrical amplitude resulting in a beneficial effect for a patient and a second electrical amplitude resulting in a side-effect for the patient.

Example 10. The system of example 1, further comprising an implantable medical device configured to deliver the electrical stimulation therapy.

Example 11. A method comprising: determining, for each respective set of electrodes of a plurality of sets of electrodes, a score based on a ratio of an electrical efficiency for the respective set of electrodes to a therapeutic window for the respective set of electrodes; determining, based on the score of each respective set of electrodes, a ranking of the plurality of sets of electrodes; and selecting, based on the ranking, a subset of the plurality of sets of electrodes for delivery of electrical stimulation therapy.

Example 12. The method of example 11, wherein the plurality of sets of electrodes is a second plurality of sets of electrodes, the method further comprising: assigning, based on a reference direction relative to a patient's anatomy and/or a sensed signal source, a primary direction to each respective set of electrodes of a first plurality of sets of electrodes; determining, based on a target location, a location of each respective set of electrodes of the first plurality of sets of electrodes; and excluding, based on the determined location and the assigned primary direction, at least one set of electrodes of the first plurality of sets of electrodes from the second plurality of sets of electrodes, wherein the second plurality of sets of electrodes does not include the excluded at least one set of electrodes.

Example 13. The method of example 12 further comprising: determining a directional orientation of a reference set of electrodes relative to a patient's anatomy during an implantation procedure or programming session, wherein the reference direction is based on the directional orientation of the reference set of electrodes to anatomy or the sensed signal source, wherein each respective electrode is an electrode set.

Example 14. The method of example 12 further comprising: prior to determining the score: assigning, based on the reference direction, a secondary direction to each respective set of electrodes of the first plurality of sets of electrodes; and excluding the at least one set of electrodes from the first plurality of sets of electrodes by excluding, based on the determined location and the assigned secondary direction, the at least one set of electrodes of the first plurality of sets of electrodes from the second plurality of sets of electrodes.

Example 15. The method of example 14 further comprising: assigning, based on the ranking, a locus set of electrodes for at least one of the primary direction or the secondary direction; and selecting, based on the locus set of electrodes, the subset of electrodes from the second plurality of sets of electrodes.

Example 16. The method of example 15 further comprising: controlling a medical device to deliver the electrical stimulation therapy via a stimulation set of electrodes including only the locus electrode; determining a reduction in symptoms or an increase of a side-effect in response to the delivered electrical stimulation; and repeatedly adding, based on the reduction in symptoms or the non-induction in increase of the side-effect, at least one other set of electrodes from the subset of electrodes to the stimulation set of electrodes, deliver electrical stimulation via the stimulation set of electrodes, and determine a reduction in symptoms or an increase of a side-effect is induced in response to the delivered electrical stimulation.

Example 17. The method of example 15 further comprising: controlling a medical device to deliver the electrical stimulation therapy via a stimulation set of electrodes including the subset of electrodes; determining based on a reduction in symptoms or a decrease of a side-effect in response to the delivered electrical stimulation; and repeatedly removing, based on the reduction in symptoms or the decrease of the side-effect, at least one other set of electrodes from the stimulation set of electrodes, deliver electrical stimulation via the stimulation set of electrodes, and determine a reduction in symptoms or a decrease of a side-effect in response to the delivered electrical stimulation.

Example 18. The method of example 11 further comprising: determining the electrical efficiency for the each respective set of electrodes based on a minimum electrical amplitude of the respective set of electrodes that results in a beneficial effect for a patient; and determining the therapeutic window for the each respective set of electrodes is based on a difference between a first electrical amplitude resulting in a side-effect for a patient and a second electrical amplitude resulting in a beneficial effect for the patient.

Example 19. A computer-readable storage medium comprising instructions that, when executed, cause processing circuitry to: determine, for each respective set of electrodes of a plurality of sets of electrodes, a score based on a ratio of an electrical efficiency for the respective set of electrodes to a therapeutic window for the respective set of electrodes; determine, based on the score of each respective set of electrodes, a ranking of the plurality of sets of electrodes; and select, based on the ranking, a subset of the plurality of sets of electrodes for delivery of electrical stimulation therapy.

Example 20. The computer-readable storage medium of example 19 further comprising instructions that, when executed, cause the processing circuitry to: assign, based on a reference direction relative to a patient's anatomy and/or a sensed signal source, a primary direction to each respective set of electrodes of a first plurality of sets of electrodes; determine, based on a target location, a location of each respective set of electrodes of the first plurality of sets of electrodes; exclude, based on the determined location and the assigned primary direction, at least one set of electrodes of the first plurality of sets of electrodes from the second plurality of sets of electrodes, wherein the second plurality of sets of electrodes does not include the excluded at least one electrode; assign, based on the reference direction, a secondary direction to each respective set of electrodes of the first plurality of sets of electrodes; exclude at least one set of electrodes from the first plurality of sets of electrodes by excluding, based on the determined location and the assigned secondary direction, at least one set of electrodes of the first plurality of sets of electrodes from the second plurality of sets of electrodes; assign, based on the ranking, a locus set of electrodes for at least one of the primary direction or the secondary direction; select, based on the locus set of electrodes, a the subset of electrodes from the second plurality of electrodes; control a medical device to deliver the electrical stimulation therapy via a stimulation set of electrodes including only the locus set of electrodes; determine a reduction in symptoms or an increase of a side-effect in response to the delivered electrical stimulation; and repeatedly add, based on the reduction in symptoms or the non-induction in increase of the side-effect, at least one other set of electrodes from the subset of electrodes to the stimulation set of electrodes, deliver electrical stimulation via the stimulation set of electrodes, and determine a reduction in symptoms or an increase of a side-effect is induced in response to the delivered electrical stimulation.

The techniques described in this disclosure may be implemented, at least in part, in hardware, software, firmware or any combination thereof. For example, various aspects of the described techniques may be implemented within one or more processors, such as fixed function processing circuitry and/or programmable processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a DVD, a floppy disk, a cassette, magnetic media, optical media, or other computer readable media.

Various examples have been described. These and other examples are within the scope of the following claims.

What is claimed is:

1. A system comprising:
a plurality of sets of electrodes configured to deliver electrical stimulation therapy; and
processing circuitry configured to:
determine, for each respective set of electrodes of the plurality of sets of electrodes, a score based on a ratio of an electrical efficiency for the respective set of electrodes to a therapeutic window for the respective set of electrodes, wherein the electrical efficiency for each respective set of electrodes is based on a minimum electrical energy applied by the respective set of electrodes that results in a beneficial effect for a patient, and wherein the therapeutic window for each respective set of electrodes is based on a difference between a first electrical energy resulting in the beneficial effect for the patient and a second electrical energy resulting in a side-effect for the patient;
determine, based on the score of each respective set of electrodes, a ranking of the plurality of sets of electrodes;
select, based on the ranking, a subset of the plurality of sets of electrodes for delivery of electrical stimulation therapy; and
control a medical device to deliver the electrical stimulation therapy via the subset of the plurality of sets of electrodes.

2. The system of claim 1, wherein the plurality of sets of electrodes is a second plurality of sets of electrodes, and wherein the processing circuitry is further configured to, prior to determining the score:
assign, based on a reference direction relative to a patient's anatomy and/or a sensed signal source, a primary direction to each respective set of electrodes of a first plurality of sets of electrodes;
determine, based on a target location, a location of each respective set of electrodes of the first plurality of sets of electrodes; and
exclude, based on the determined location and the assigned primary direction, at least one set of electrodes of the first plurality of sets of electrodes from the second plurality of sets of electrodes, wherein the second plurality of sets of electrodes does not include the excluded at least one set of electrodes.

3. The system of claim 2, wherein the processing circuitry is further configured to:
determine a directional orientation of a reference set of electrodes relative to a patient's anatomy during an implantation procedure or programming session, wherein the reference direction is based on the directional orientation of the reference set of electrodes to anatomy or the sensed signal source.

4. The system of claim 2, wherein the processing circuitry is further configured to, prior to determining the score:
assign, based on the reference direction, a secondary direction to each respective set of electrodes of the first plurality of electrodes; and
exclude the at least one set of electrodes from the first plurality of sets of electrodes by excluding, based on the determined location and the assigned secondary direction, the at least one set of electrodes of the first plurality of sets of electrodes from the second plurality of sets of electrodes.

5. The system of claim 4, wherein the processing circuitry is further configured to:
assign, based on the ranking, a locus set of electrodes for at least one of the primary direction or the secondary direction; and
select, based on the locus set of electrodes, the subset of electrodes from the second plurality of sets of electrodes.

6. The system of claim 5, wherein the processing circuitry is further configured to:
control a medical device to deliver the electrical stimulation therapy via a stimulation set of electrodes including only the locus electrode;

determine a reduction in symptoms or an increase of the side-effect in response to the delivered electrical stimulation; and repeatedly add, based on the lack of reduction in symptoms or the non-induction of increase in the side-effect, at least one other set of electrodes from the subset of electrodes to the stimulation set of electrodes, deliver electrical stimulation via the stimulation set of electrodes, and determine a reduction in symptoms or an increase of the side-effect is induced in response to the delivered electrical stimulation.

7. The system of claim 5, wherein the processing circuitry is further configured to:

control a medical device to deliver the electrical stimulation therapy via a stimulation set of electrodes including the subset of electrodes;

determine based on a reduction in symptoms or a decrease of the side-effect in response to the delivered electrical stimulation; and repeatedly remove, based on the reduction in symptoms or the decrease of the side-effect, at least one other set of electrodes from the stimulation set of electrodes, deliver electrical stimulation via the stimulation set of electrodes, and determine a reduction in symptoms or a decrease of the side-effect in response to the delivered electrical stimulation.

8. The system of claim 1, wherein the processing circuitry is further configured to:

determine the electrical efficiency for each respective set of electrodes based on a minimum electrical amplitude of the respective set of electrodes that results in the beneficial effect for a patient.

9. The system of claim 1, wherein the processing circuitry is further configured to:

determine the therapeutic window for each respective set of electrodes is based on a difference between a first electrical amplitude resulting in the beneficial effect for a patient and a second electrical amplitude resulting in the side-effect for the patient.

10. The system of claim 1, further comprising an implantable medical device configured to deliver the electrical stimulation therapy.

11. A method comprising:

determining, for each respective set of electrodes of a plurality of sets of electrodes, a score based on a ratio of an electrical efficiency for the respective set of electrodes to a therapeutic window for the respective set of electrodes, wherein the electrical efficiency for each respective set of electrodes is based on a minimum electrical energy applied by the respective set of electrodes that results in a beneficial effect for a patient, wherein the therapeutic window for each respective set of electrodes is based on a difference between a first electrical energy resulting in the beneficial effect for the patient and a second electrical energy resulting in a side-effect for the patient;

determining, based on the score of each respective set of electrodes, a ranking of the plurality of sets of electrodes;

selecting, based on the ranking, a subset of the plurality of sets of electrodes for delivery of electrical stimulation therapy; and controlling a medical device to deliver the electrical stimulation therapy via the subset of the plurality of sets of electrodes.

12. The method of claim 11, wherein the plurality of sets of electrodes is a second plurality of sets of electrodes, the method further comprising:

assigning, based on a reference direction relative to a patient's anatomy and/or a sensed signal source, a primary direction to each respective set of electrodes of a first plurality of sets of electrodes;

determining, based on a target location, a location of each respective set of electrodes of the first plurality of sets of electrodes; and excluding, based on the determined location and the assigned primary direction, at least one set of electrodes of the first plurality of sets of electrodes from the second plurality of sets of electrodes, wherein the second plurality of sets of electrodes does not include the excluded at least one set of electrodes.

13. The method of claim 12 further comprising:

determining a directional orientation of a reference set of electrodes relative to a patient's anatomy during an implantation procedure or programming session, wherein the reference direction is based on the directional orientation of the reference set of electrodes to anatomy or the sensed signal source, wherein each respective electrode is an electrode set.

14. The method of claim 12 further comprising:

prior to determining the score:

assigning, based on the reference direction, a secondary direction to each respective set of electrodes of the first plurality of sets of electrodes; and excluding the at least one set of electrodes from the first plurality of sets of electrodes by excluding, based on the determined location and the assigned secondary direction, the at least one set of electrodes of the first plurality of sets of electrodes from the second plurality of sets of electrodes.

15. The method of claim 14 further comprising:

assigning, based on the ranking, a locus set of electrodes for at least one of the primary direction or the secondary direction; and selecting, based on the locus set of electrodes, the subset of electrodes from the second plurality of sets of electrodes.

16. The method of claim 15 further comprising:

controlling a medical device to deliver the electrical stimulation therapy via a stimulation set of electrodes including only the locus electrode;

determining a reduction in symptoms or an increase of the side-effect in response to the delivered electrical stimulation; and repeatedly adding, based on the reduction in symptoms or the non-induction in increase of the side-effect, at least one other set of electrodes from the subset of electrodes to the stimulation set of electrodes, deliver electrical stimulation via the stimulation set of electrodes, and determine a reduction in symptoms or an increase of the side-effect is induced in response to the delivered electrical stimulation.

17. The method of claim 15 further comprising:

controlling a medical device to deliver the electrical stimulation therapy via a stimulation set of electrodes including the subset of electrodes;

determining based on a reduction in symptoms or a decrease of the side-effect in response to the delivered electrical stimulation; and repeatedly removing, based on the reduction in symptoms or the decrease of the side-effect, at least one other set of electrodes from the stimulation set of electrodes, deliver electrical stimulation via the stimulation set of electrodes, and determine a reduction in symptoms or a decrease of the side-effect in response to the delivered electrical stimulation.

18. The method of claim 11 further comprising:
determining the electrical efficiency for each respective set of electrodes based on a minimum electrical amplitude of the respective set of electrodes that results in the beneficial effect for a patient; and
determining the therapeutic window for each respective set of electrodes is based on a difference between a first electrical amplitude resulting in the side-effect for a patient and a second electrical amplitude resulting in the beneficial effect for the patient.

19. A non-transitory computer-readable storage medium comprising instructions that, when executed, cause processing circuitry to:
determine, for each respective set of electrodes of a plurality of sets of electrodes, a score based on a ratio of an electrical efficiency for the respective set of electrodes to a therapeutic window for the respective set of electrodes, wherein the electrical efficiency for each respective set of electrodes is based on a minimum electrical energy applied by the respective set of electrodes that results in a beneficial effect for a patient, wherein the therapeutic window for each respective set of electrodes is based on a difference between a first electrical energy resulting in the beneficial effect for the patient and a second electrical energy resulting in a side-effect for the patient;
determine, based on the score of each respective set of electrodes, a ranking of the plurality of sets of electrodes;
select, based on the ranking, a subset of the plurality of sets of electrodes for delivery of electrical stimulation therapy; and
controlling a medical device to deliver the electrical stimulation therapy via the subset of the plurality of sets of electrodes.

20. The computer-readable storage medium of claim 19 further comprising instructions that, when executed, cause the processing circuitry to:

assign, based on a reference direction relative to a patient's anatomy and/or a sensed signal source, a primary direction to each respective set of electrodes of a first plurality of sets of electrodes;
determine, based on a target location, a location of each respective set of electrodes of the first plurality of sets of electrodes;
exclude, based on the determined location and the assigned primary direction, at least one set of electrodes of the first plurality of sets of electrodes from the second plurality of sets of electrodes, wherein the second plurality of sets of electrodes does not include the excluded at least one electrode;
assign, based on the reference direction, a secondary direction to each respective set of electrodes of the first plurality of sets of electrodes;
exclude the at least one set of electrodes from the first plurality of sets of electrodes by excluding, based on the determined location and the assigned secondary direction, the at least one set of electrodes of the first plurality of sets of electrodes from the second plurality of sets of electrodes;
assign, based on the ranking, a locus set of electrodes for at least one of the primary direction or the secondary direction;
select, based on the locus set of electrodes, the subset of electrodes from the second plurality of electrodes;
control a medical device to deliver the electrical stimulation therapy via a stimulation set of electrodes including only the locus set of electrodes;
determine a reduction in symptoms or an increase of the side-effect in response to the delivered electrical stimulation; and
repeatedly add, based on the reduction in symptoms or the non-induction in increase of the side-effect, at least one other set of electrodes from the subset of electrodes to the stimulation set of electrodes, deliver electrical stimulation via the stimulation set of electrodes, and determine a reduction in symptoms or an increase of the side-effect is induced in response to the delivered electrical stimulation.

* * * * *